US012178591B2

(12) United States Patent
Mahon et al.

(10) Patent No.: US 12,178,591 B2
(45) Date of Patent: Dec. 31, 2024

(54) SYSTEM FOR ESTIMATING BRAIN INJURY

(71) Applicant: Carnegie Mellon University, Pittsburgh, PA (US)

(72) Inventors: Bradford Mahon, Pittsburgh, PA (US); Adnan Hirad, Rochester, NY (US)

(73) Assignee: Carnegie Mellon University, Pittsburgh, PA (US)

( * ) Notice: Subject to any disclaimer, the term of this patent is extended or adjusted under 35 U.S.C. 154(b) by 84 days.

(21) Appl. No.: 17/395,247

(22) Filed: Aug. 5, 2021

(65) Prior Publication Data
US 2022/0039732 A1 Feb. 10, 2022

Related U.S. Application Data

(60) Provisional application No. 63/061,216, filed on Aug. 5, 2020.

(51) Int. Cl.
*A61B 5/00* (2006.01)
*A61B 5/301* (2021.01)

(52) U.S. Cl.
CPC .......... *A61B 5/4064* (2013.01); *A61B 5/0004* (2013.01); *A61B 5/0053* (2013.01);
(Continued)

(58) Field of Classification Search
CPC ... A61B 5/6814; A61B 5/1114; A61B 5/4064; A61B 5/6832; A61B 5/6803; A61B 2562/0219; A61B 5/0053; A61B 5/11; A61B 5/682; A61B 5/0263; A61B 5/4076; A61B 5/7275; A61B 5/0042; A61B 5/055; A61B 5/0004; A61B 5/301; A61B 5/7264;
(Continued)

(56) References Cited

U.S. PATENT DOCUMENTS

2017/0069223 A1* 3/2017 Cramer ................. A63F 13/218
2018/0110466 A1* 4/2018 Ralston ................ A61B 5/1114
(Continued)

OTHER PUBLICATIONS

Tamara C. Valovich McLeod, Joy H. Lewis, Kate Whelihan, Cailee E. Welch Bacon; Rest and Return to Activity After Sport-Related Concussion: A Systematic Review of the Literature. J Athl Train Mar. 1, 2017; 52 (3): 262-287. doi: doi.org/10.4085/1052-6050-51.6.06 (Year: 2017).*

*Primary Examiner* — Matthew Kremer
*Assistant Examiner* — Elina Sohyun Ahn
(74) *Attorney, Agent, or Firm* — Fish & Richardson P.C.

(57) ABSTRACT

A system is configured for receiving force data including at least one value indicating the amount of the force applied to the portion of the user and at least one value indicating a direction of the force applied to the portion of the user; obtaining mapping data specifying at least one relation between values of force applied to the portion of the user and changes in a functional responsiveness, functional and/or structural integrity, or both the functional responsiveness and the functional and/or structural integrity of the brain at one or more locations in the brain; estimating, based on the mapping data and the force data, an amount of force loading at one or more particular locations in the brain; and generating, based on the estimating, output data representing an amount of the damage to the brain at the one or more particular locations in the brain.

26 Claims, 13 Drawing Sheets

(52) U.S. Cl.
CPC ............ *A61B 5/301* (2021.01); *A61B 5/6803* (2013.01); *A61B 5/7264* (2013.01); *A61B 5/7275* (2013.01); *A61B 5/746* (2013.01); *A61B 2562/0219* (2013.01)

(58) Field of Classification Search
CPC ... A61B 5/746; G01L 5/0052; A63B 2220/40; A63B 2220/53; G01P 15/18; G01N 33/6896; G01N 2800/28; G01N 33/50; G01N 33/53; C07K 14/4713; C07K 14/475; C07K 14/47; C12N 9/88; C12Y 402/01011; G06T 7/0014; G06T 5/50; G06T 7/11; G06T 2207/10088; G06T 2207/20212; G06T 2207/30016; G01R 33/4806; G01R 33/5608; G16H 30/40; G16H 50/20; G16H 50/50
See application file for complete search history.

(56) References Cited

U.S. PATENT DOCUMENTS

| | | | | |
|---|---|---|---|---|
| 2019/0320965 | A1* | 10/2019 | Ng | A61B 5/7282 |
| 2020/0230008 | A1* | 7/2020 | Newham | A61B 5/6894 |
| 2020/0312461 | A1* | 10/2020 | Bartsch | G01P 15/0891 |
| 2021/0085209 | A1* | 3/2021 | Papageorgiou | A61B 5/0042 |
| 2022/0074953 | A1* | 3/2022 | Van Meter | G01N 33/6896 |
| 2022/0148181 | A1* | 5/2022 | Murray | G01R 33/5608 |
| 2022/0248980 | A1* | 8/2022 | Devani | A61B 5/1115 |

* cited by examiner

SYSTEM FOR ESTIMATING BRAIN INJURY

CLAIM OF PRIORITY

This application claims priority under 35 U.S.C. § 119(e) to U.S. Patent Application Ser. No. 63/061,216, filed on Aug. 5, 2020, the entire contents of which are hereby incorporated by reference.

GOVERNMENT SUPPORT CLAUSE

This invention was made with United States government support under grant number NS089609 awarded by the National Institutes of Health. The U.S. Government has certain rights in the invention.

TECHNICAL FIELD

This disclosure relates to wearable technologies and machine learning models or AI models.

BACKGROUND

Chronic traumatic encephalopathy (CTE) is a neurodegenerative disease associated with exposure to repetitive head impacts. Functions of the brain are related to symptoms and signs of concussion, or mild traumatic brain injury (mTBI). mTBI is clinically defined as a "the rapid onset of short-lived impairment of neurological function that resolves spontaneously . . . caused either by a direct blow to the head, face, neck or elsewhere on the body with an 'impulsive' force transmitted to the head." Currently return-to-play or return-to-battle decisions are based on whether an individual exhibits clinical signs and symptoms or mTBI. By the time a subject exhibits signs of concussion or mTBI, an injury may have accumulated that will have long-term effects on the health of the user.

SUMMARY

This disclosure describes a system for estimating brain injury resulting from detected forces applied to a person. The system is configured to measure forces that are applied to a head or body of a person and estimate effects of the force on one or more regions of interest (ROI) in the brain of the person. The system determines whether the forces experienced create risks for causing any damage to the brain of the person. Brain damage is associated with one or more changes in a structure of the brain, such as a reduced white matter integrity, or to changes in the function of the brain that may not be detectable as structural alterations. Here, estimating brain injury includes inferring injury or determining a probability or likelihood of brain injury. As described herein, the system is configured to estimate an amount of damage to the brain of a user of the system, even when the damage does not result in observable symptoms or clinical signs in the user.

The systems and processes described in this document enable one or more of the following advantages. Brain injury that is sub-concussive or asymptomatic can be identified for a user of the wearable device in real-time or near real-time. Here, real-time or near real-time refers to a determination of the brain injury within a few seconds or minutes after the wearer of the wearable device is impacted by forces that cause brain injury. The brain injury can be determined, and the user alerted before the user experiences additional forces that may worsen the brain injury or cause new injury. The brain injury can be estimated without requiring the user to undergo an MM or other extensive imaging or analysis of the brain, but rather includes only motion data from motions sensors (such as accelerometers or transducers) that are coupled to the wearable device(s) that the user is wearing.

The one or more advantages previously described can be enabled by one or more embodiments.

In a general aspect, a system for detecting an injury to a brain, the injury being caused by a force applied to portion of a user, the system comprising: at least one sensor configured to output force data specifying the force applied to the portion of the user; at least one processing device configured for communication with the at least one sensor; and a memory storing instructions that, when executed by the at least one processing device, cause the at least one processing device to perform operations. The operations include receiving the force data from the sensor, the force data including at least one value indicating the amount of the force applied to the portion of the user and at least one value indicating a direction of the force applied to the portion of the user; obtaining mapping data specifying at least one relation between values of force applied to the portion of the user and changes in a functional responsiveness, functional and/or structural integrity, or both the functional responsiveness and the functional and/or structural integrity of the brain at one or more locations in the brain; estimating, based on the mapping data and the force data, an amount of force loading at one or more particular locations in the brain; and generating, based on the estimating, output data representing an amount of the damage to the brain at the one or more particular locations in the brain.

In some implementations, the operations further include obtaining prior damage data representing a prior amount of damage estimated for the particular location in the brain over a predetermined period of time; generating a cumulative damage estimate by combining the amount of damage of the output data and the prior amount of damage; comparing the cumulative damage estimate at each location in the brain to a threshold that is specific to that location; and generating an alert when the cumulative damage estimate satisfies the threshold or is projected to satisfy the threshold, the alert indicating a safety warning.

In some implementations, the amount of damage to the brain represents a change in the structural and/or functional integrity of the brain or the functional responsiveness at the particular location relative to an initial or normative white matter integrity value at the particular location.

In some implementations, the at least one value of the force applied to the portion of the user comprises an azimuth value, elevation value, or combination of the azimuth value and elevation value.

In some implementations, the operations further include: obtaining prior damage data representing a prior amount of damage estimated for the particular location in the brain at a first time; obtaining time data indicative of a second time associated with the force data; weighting the prior amount of damage based on a difference between the first time and the second time or compared to a normative measure of structural or functional integrity to generate weighted damage data; and generating a cumulative damage estimate by combining the weighted damage data and the amount of damage of the output data.

In some implementations, weighting the prior amount of damage comprises adjusting an estimated reduction in brain structural, material, or functional integrity as a function of the difference between the first time and the second time or compared to normative measure of brain structure and function, stratified by one or more demographic parameters describing a user.

In some implementations, obtaining the mapping data comprises: accessing a machine learning model configured to generate the mappings, the machine learning model comprising a plurality of weight values, wherein one or more weight values of the plurality correspond to the one or more locations in the brain, and wherein each mapping between a given value of force applied to the portion of the user and a given change in the structural integrity or the functional responsiveness of the brain is based on at least one weight value of the plurality of weight values.

In some implementations, the machine learning model is trained using associations between magnetic resonance imaging (MM) data and fingerprints of the force data, the MRI data representing values for one or more features of the brain, and the fingerprints of the force data representing values for one or more features of rotational force, translational force, or a combination of rotational and translational forces.

In some implementations, the values of the features of the brain are based on a diffusion tensor or fiber orientation distribution model, a measure of grey matter thickness, or a measure of non-directional diffusion properties including mean diffusivity, applied to voxels of the MM data, and wherein the features comprise one or more of a fractional anisotropy (FA) map, a mean diffusivity (MD) map, a radial diffusivity (RD) map, an axial diffusivity (AD) map or an apparent fiber density (AFD) map.

In some implementations, the machine learning model is trained by performing operations comprising: receiving data from Magnetic Resonance Elastography (MRE) and related protocols such as slip interface imaging (SII) representing a measurement of a location of a force concentration due to inherent material property characteristics of a region in the brain or boundary conditions between this region and its adjacent structures in the brain that is mapped to a location of the force on the portion of the user; and minimizing, based on the MRE data, a difference between a predicted damage to the brain based on the machine learning model and a measured damage to the brain from Mill data, the minimizing comprising updating one or more weight values of the plurality of weight values.

In some implementations, the one or more locations are defined by performing operations comprising: obtaining first mask data representing a defined region of the brain: obtaining second mask data representing a midbrain region of interest; identifying voxels representing regions of intersection of the first mask data and the second mask data; and defining the one or more locations at the regions of intersection of different regions or structures of the brain.

In some implementations, the system further comprises a hardware indictor, and the operations further comprise: causing the hardware indicator to activate in response to generating the output data.

In some implementations, the at least one sensor comprises of a transducer or an accelerometer.

In some implementations, the force data comprises a representation of rotational force sustained by the brain, a representation of translational force sustained by the brain, or a combination of the translational force and the rotational force.

In some implementations, the at least one sensor is coupled to a wearable device configured to be worn by a person.

In some implementations, the force data represents a sub-concussive impact or an asymptomatic impact to the portion of the user as well as symptomatic impact or concussive impact to the portion of the user.

In some implementations, the at least one processing device is part of a cloud computing platform.

In some implementations, the amount of damage to the brain represents an estimate of a breakdown in a blood-brain barrier of the brain.

In some implementations, generating the output data representing the amount of the damage to the brain at the particular location in the brain comprises transmitting the output data to a remote device.

In some implementations, generating output data representing the amount of the damage to the brain at the particular location in the brain occurs in real-time or near real-time to enable a user to take an action to prevent an additional amount of the damage to the brain.

In some implementations, the force data represents a physical hit on the portion of the user, a whiplash from a body hit, a blast force applied to the portion of the user, or a combination of the physical hits and the blast force.

In some implementations, the operations further include validating the output data using a rheological process including analysis of a cadaveric brain materials or a three-dimensional printed non-biological material.

In some implementations, the operations further include generating a prediction of an amount of time for the user to rest before further exposure to forces.

In a general aspect, a method for detecting an injury to a brain, the injury being caused by a force applied to portion of a user, includes receiving the force data from the sensor, the force data including at least one value indicating the amount of the force applied to the portion of the user and at least one value indicating a direction of the force applied to the portion of the user; obtaining mapping data specifying at least one relation between values of force applied to the portion of the user and changes in a functional responsiveness, functional and/or structural integrity, or both the functional responsiveness and the functional and/or structural integrity of the brain at one or more locations in the brain; estimating, based on the mapping data and the force data, an amount of force loading at one or more particular locations in the brain; and generating, based on the estimating, output data representing an amount of the damage to the brain at the one or more particular locations in the brain. The method can be combined with one or more of the implementations described herein.

In a general aspect, one or more non-transitory computer readable media store instructions for detecting an injury to a brain, the injury being caused by a force applied to portion of a user. The instructions, when executed by the at least one processing device, cause the at least one processing device to perform operations. The operations include receiving the force data from the sensor, the force data including at least one value indicating the amount of the force applied to the portion of the user and at least one value indicating a direction of the force applied to the portion of the user; obtaining mapping data specifying at least one relation between values of force applied to the portion of the user and changes in a functional responsiveness, functional and/or structural integrity, or both the functional responsiveness and the functional and/or structural integrity of the brain at one or more locations in the brain; estimating, based on the mapping data and the force data, an amount of force loading at one or more particular locations in the brain; and generating, based on the estimating, output data representing an amount of the damage to the brain at the one or more particular locations in the brain. The one or more non-transitory computer readable media can be combined with one or more of the implementations described herein.

The details of one or more implementations are set forth in the accompanying drawings and the description below. Other features and advantages will be apparent from the description and drawings, and from the claims.

DETAILED DESCRIPTION

Figure 1:
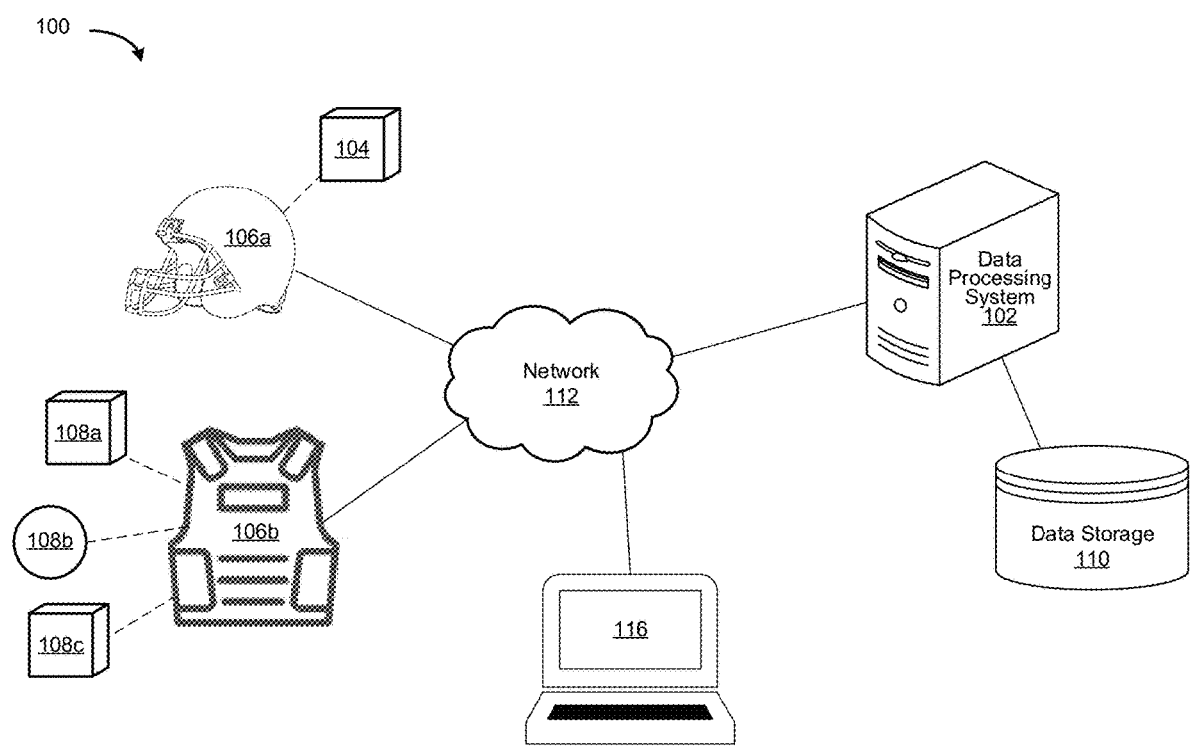
FIG. 1 shows an example system for detecting brain injury resulting from force applied to a person.

FIG. 1 shows an example system 100 for detecting brain injury resulting from force applied to a person. The system 100 is configured to measure forces that are applied to a head or body of a person and estimate effects of the force on one or more regions of interest (ROI) in the brain of the person. The system 100 determines whether the force causes any damage to the brain of the person. Brain damage is associated with one or more changes in a structure of the brain, such as a reduced white matter integrity, or a change in the functioning of the brain. As described herein, the system 100 is configured to estimate an amount of damage to the brain of a user of the system, even when the damage does not result in observable symptoms in the user (e.g., asymptomatic brain damage). The system 100 is configured to monitor damage to the user's brain as the user experiences forces to the head or body over time. The system 100 is configured to estimate a total damage level or damage severity over time, for each specified region of the brain. The system 100 is configured to generate data that alerts a user of the system to the amount of estimated brain damage. As described herein, the system 100 generates an alert if a user has experienced an estimated brain damage over a threshold, such as brain damage that may cause permanent brain injury if further forces are experienced. As described herein, the system 100 is configured to generate (e.g., compute) estimates of brain damage of the user and report the estimate in real-time, such as within a few seconds or minutes of the forces being experienced by the user.

The system 100 includes a wearable device 106 (such as wearable devices 106a, 106b shown in FIG. 1). One or more force measuring sensors (such as one or more of sensors 104, 108a-c) is coupled to the wearable device 106. The one or more sensors 104, 108a-c coupled to the wearable device 106 are each configured to measure forces exerted on the wearable device 106, and thus a wearer of the wearable device, and generate data representing the force(s). The system 100 includes a data processing system 102 configured to process the sensor data including the measured forces, as described herein, and estimate an amount of brain damage experienced by the wearer of the wearable device 106. The wearable device 106 can include circuitry (e.g., a transmitter, transceiver, etc.) configured to transmit the sensor data over a network (e.g., Wi-Fi, Bluetooth etc.) 112 to the data processing system 102, as described herein, for real-time estimation and reporting of estimated brain damage.

The wearable device 106 of the system 100 can include any device wearable by a user that can support one or more of the force measuring sensors (e.g., sensors 104, 108a-c). For example, the wearable device 106 can include a helmet 106a with one or more force measuring sensors, such as sensor 104, mounted in or on the helmet. In an example, the helmet 106a is configured to be worn over the head of a user of the helmet. The helmet 106a is rigid or semi-rigid such that forces exerted on the helmet (such as a blunt impact or blast force) are measured by the sensor 104. In another example, the wearable device 106 of the system 100 can include a vest 106b or similar clothing that is wearable on a body of the user. The vest 106b can include padding (such as a rigid shell form coupled to soft pads), a flak vest, or any other wearable configured to support one or more sensors 108a-c on the body of the user. While three sensors 108a-c are shown, the number of sensors can be one or more sensors. The sensors 108a-c are placed on the vest 106b to measure forces, such as blast forces or impact forces, on the user who is wearing the vest. In some implementations, the wearable is another device that is configured to work on the user with any number of sensors.

To reduce rotational forces and thus rotational velocities of the helmeted head modifications to a helmet can be made. This can apply to all impact scenarios including but not limited to helmet-to-helmet, helmet-to-body and helmet-to-ground impacts by optimizing the weight and geometry (and shape) of the helmet. Such a design achieves reduction in rotational acceleration and linear acceleration of the head in all impact scenarios by 1) optimizing moment of inertia associated with helmets by reducing helmet weights to 1 lb. and 2) reshaping the geometry of the helmet to reduce the in-air angular velocities of the helmeted-head in impending helmet-to-ground impact scenarios, 3) outside of the helmet is designed to absorb rotational forces and not transmit them to the head. Padding is added the outside of the helmet, or shock absorbers connecting the internal padding to the external shell of the helmet using shear-thinning polymers on the outer shell. These helmet modifications (e.g., to existing football helmets) reduces the transmission of impact-related shear waves to the midbrain (and brainstem) as well as the corpus callosum, in comparison to existing helmets.

Any of the sensors 104, 108a-c include sensing devices configured to measure forces experienced by the sensors.

The forces can include blast forces that are indirect forces in which there is no physical impact but a pressure wave or blast wave impacting the sensor. The forces can include impact forces including a direct impact to the sensor. The sensors 104, 108a-c can include accelerometers, gyroscopes, transducers (such as load cells or acoustic transducers), and so forth, or a combination thereof.

The sensors 104, 108a-c each generate data representing an angle of the force on the wearable device 106. For example, the sensor data can include azimuth and elevation data that together specify a particular direction of the force received by the wearable device 106 in the coordinate system of the sensor. The sensor data includes magnitude data indicating the magnitude of the force received by the wearable device 106. In some implementations, the force is measured as a linear acceleration (gravitational forces) and rotational acceleration (radians per squared seconds).

Each of the sensors 104, 108a-c is configured to provide data to the data processing system 102 via circuitry on the wearable devices 106a-b. In some implementations, the data processing system 102 is remote from the wearable devices 106, as shown in FIG. 1. In this example, the data processing system 102 is configured to receive the sensor data from the sensors 104, 108a-c as a data stream or in intermittent transmissions from the wearable device(s). The data processing system 102 can include a cloud computing system. The data processing system 102 receives the data from the wearable device 106 over the network 112, processes the sensor data using one or more machine learning models (or artificial intelligence models) as described herein, and outputs a result including a estimation of whether a user of the wearable device 106 is experiencing brain damage and/or an estimate of an amount of brain damage (even if asymptomatic or at a low level). In this application, machine learning models include both strict machine learning and, more broadly, algorithms for artificial intelligence outside of machine learning models. For example, the approaches here can include both machine learning model classification models and artificial intelligences such as Bayesian approaches, symbolic logic, rule based systems, and so forth. For example, mappings between the forces received by the user of the wearable 106 and force loadings on locations of the brain can be conditionalized on discrete variables or decision trees across variables. One example of this may be to integrate results of clinical exams and discrete diagnoses into the procedures for updating weights of force loadings in the brain to improve the ability of the technology to predict future clinical exams. For instance, if an individual exhibited oculomotor dysfunction (eye movement problems) after a head hit, then that information could be used to increase the gain on weights in parts of the brain that are independently known to support eye movements.

The data processing system 102 can transmit the output data over the network 112 to a client device 116 configured to present the output estimate to a user. In some implementations, the data processing system 102 stores the estimate in a related data storage 110 for updating one or more machine learning models or for one or more other applications. For example, the data processing system 102 can use an output estimate for a particular wearable device 106, from a given time period, in combination with other output data associated with the particular wearable device 106 from other time periods. In another example, the data processing system 102 can combine data from a first wearable device, such as device 106a, with data from a second wearable device 106b. The data processing system 102 can combine data from multiple wearable devices 106a-b for generating combined output estimation data using input data from both wearable devices 106a-b. For example, a user can be wearing both the helmet 106a and the vest 106b, and data from each of sensors 104, 108a-b can be combined for generation of the output estimate. In another example, the data processing system 102 receives data from multiple wearable devices 106a-b and combines these data for presentation of output estimation data after the estimate is generated for each wearable device 106a-b. For example, the data processing system 102 can generate a visualization of estimated brain damage for each member of a group of users (sports team, army platoon, etc.) each wearing an instance of one or more wearable devices 106a-b. The data processing system 102 and client device 116 together enable continuous or nearly continuous monitoring of the group of users to determine if any of the users is experiencing damage to the brain.

The client device 116 generally includes a device usable by an end-user for accessing data of the system 100 or portions thereof. The client device can include a laptop computer, desktop computer, mobile phone, tablet, wearable device, or any similar computing device. In some implementations, the data processing system 102 is hosted by the client device 116. The client device 116 includes a user interface for presentation of output data including estimates of brain damage for a user wearing the wearable device 106. For example, a push notification can be generated and presented on the client device 116 for alerting the user of the client device that the wearer of the wearable device 106 has exceeded a damage threshold.

In some implementations, the client device 116 can be a part of the wearable device 106. For example, the client device 116 can include a computing device that is coupled to the wearable device (such as a smart watch, bracelet, belt, etc.) that is configured to output presentation data generated by the data processing system 102. For example, the wearable device can emit a sound (such a tone) when a wearer of the device has experienced forces that cause damage exceeding a threshold. In another example, the client device 116 worn by the user can flash a color or emit a tone indicating an amount of the damage received over time. For example, the screen of a device may be green and progress to red as the user experiences more force causing brain injury over time. Other similar examples are possible.

The data processing system 102 is configured to execute one or more machine learning or artificial intelligence (AI) models for generating an estimate of a brain injury to a user or recovery/rest time before the user should experience additional forces. To generate the estimate, the data processing system 102 is configured to assign force loadings to brain areas using a mapping generated based on the machine learning models or AI models. The data processing system 102 is then configured to infer an injury to the brain caused by the force loadings (or forces experienced) by those regions of the brain. The actual amount of damage or injury to the brain is an estimated value, rather than a measured value. The damage or injury to the brain refers to a breakdown of structure in the brain, such as damage to a blood-brain-barrier or a reduction in white matter integrity, or a change in the functioning of the brain.

Recovery or rest time can be estimated in the same way using AI/ML models trained over prior data. For example, machine learning models or AI models can generate mappings for a recovery of the brain in response to receiving force loadings over time. Subsequent forces to the brain incur greater injury than initial forces. Over time, the brain recovers from this risk (though the injury may still be present). The amount of time to wait depends on the force loadings experienced at various locations in the brain. The model can generate predictions or estimations of how long a user should recover from a given amount of force loadings to the brain for the user to have reduced or eliminated increased risk of additional brain injury from those initial forces. For example, the user receives forces at time T1. Based on the estimated force loadings at each location in the brain (using the machine learning models described herein), the data processing system 102 predicts that the user should wait a time period (e.g., several hours, several days, several months, etc.) before increased risk of brain injury is reduced or eliminated from the user having experienced those forces.

The regions of the brain, also called locations or regions of interest (ROI), are locations in the brain that are associated with brain injury when brain structures/functions in those regions are damaged. These locations are mapped to data from the sensors 104, 108a-c. When data having particular values (e.g., particular data signature or data fingerprint) is measured, the forces are mapped to particular force loads on each of the regions of interest or locations of the brain. The machine learning models or AI models, as described herein, are used to determine a relationship between force values measured by the sensors 104, 108a-c and the values of force loadings on the regions of brain. The values of the force loadings on the regions of the brain are mapped to an estimate of how much such injury there is to the brain.

The data processing system 102 hosts machine learning models or AI models that are trained on magnetic resonance imaging (MM) data, accelerometer data, and other data such as magnetic resonance elastography (MRE) data. The machine learning model is trained with data including sensor data including particular force values (e.g., data fingerprints or data signatures), such as particular elevation and azimuth values associated with forces and their magnitudes, that are associated with particular locations of force loading in the brain. The association is made by pairing the sensor data signature with MM data images showing measured changes to brain structure or brain function as a result of experiencing those force values in the sensor data.

The output of the machine learning process includes a weight matrix (or weight matrices) that associate features of accelerometer data with amounts of injury to the brain, and by inference predicted return to activity and/or recovery time. The machine learning model associates locations on the skull or head (or body) of a user that experience force with an amount of brain injury at the regions of interest in the brain. The machine learning model therefore maps force loadings measured by the sensors 104, 108a-c to brain regions of interest. Using data of the MM, the data processing system 102 is configured to generate an inference of injury loading caused by those force loadings at the locations. The weights of the weight matrices represent the mapping of the locations of the forces experienced on the skull or head to the inferred brain injury. When the machine learning model is trained, the data processing system 102 is configured to generate an estimate (e.g., a prediction or inference) of the amount of brain damage or brain injury and predicted recovery time based on the measured forces.

The data processing system 102 is configured to refine the machine learning models or AI models using supplemental data, such as MRE data. The MRE data includes empirical measurements of force concentrations on the brain from calibrated forces (e.g., taps) of particular magnitudes and locations that are applied to the skull or head of a user. The MRE data are used as "ground-truth" data for calibration of the machine learning models or AI models. The MRE data are used to refine the weight matrices of the machine learning model of the data processing system 102. The data processing system 102 can generate updated estimates of brain injury or brain damage using the updated weight values. The data processing system 102 updates the weight values to minimize a discrepancy between a predicted or estimated damage to each region of the brain and a measured amount of damage (e.g., from a subsequent MRI or BBB measurement) to the brain.

The mapping data of the machine learning model is generated by executing the machine learning models or AI models described herein. The mapping data maps the force data received by the accelerometer to force loadings at regions of the brain. The mapping is based on the weighting values of the weight matrix in which each weight is associated with one of the locations or regions of interest in the brain. The data processing system 102 accesses the machine learning model that is trained using the MM and/or MRE data to determine the exact values for each of the weightings. The weighting values can vary depending on with which region a particular weighting value is associated. In some implementations, each mapping between a given value of force applied to the head and a force loading in the brain is used to infer a given change in structural or functional integrity of the brain for that region.

As previously described, the machine learning model is trained using associations between MRI data and fingerprints of the force data from sensors 104, 108a-c. The MRI data represents values for one or more features of the brain associated with brain damage, as subsequently described. The fingerprints of the impact data represent values for one or more features of rotational force, translational force, or a combination of rotational and translational forces from the sensors 104, 108a-c. More specifically, a data fingerprint from the sensors 104, 108a-c includes a spatial distribution of force loadings for each impact to the body/head, where that spatial distribution can be either measured within a given individual (MRI) or inferred for a given individual (based on MRIs of prior individuals).

The MRI data can include the following types of MRI data: Structural (e.g. MPRAGE, T2, FLAIR and Diffusion-weighted MM), Functional (resting-state fMRI and Task-Based fMRI), PET-MM, and material-properties imaging (e.g. MRE and slip interphase imaging (SII)).

The values of white matter integrity of the brain can be based on directional diffusion-based measures or non-directional diffusion-based measures. Generally, diffusion tensors and fiber orientations are directional inferences generated on the basis of diffusion data. The diffusion tensors are directional because the diffusion tensors indicate the direction/orientation of white matter fibers. The directional measurements are derived from underlying diffusion measures of water in tissue (e.g., radial, axial, mean diffusivity, fractional anisotropy, apparent fiber density etc.). For example, the features can include a diffusion tensor or fiber orientation distribution model, a measure of grey matter thickness, a fractional anisotropy (FA) map, a mean diffusivity (MD) map, a radial diffusivity (RD) map, an axial diffusivity (AD) map, and/or an apparent fiber density (AFD) map.

However, non-directional based measures of structural integrity or functional integrity can be used in additional or in the alternative. For example, the feature can be based on a measure of diffusion properties that are non-directional (mean diffusivity) model applied to voxels of the MM data. The features can represent a measure of brain metabolism of specific types of proteins such in PET-MRI, or the specific functioning of brain regions such as with BOLD fMRT. The system 100 is configured for inter-operability across all of those structural and functional measures.

The data processing system 102 is configured to track cumulative forces over a period of time and thus track cumulative injury loading for various locations in the brain of the user. In some implementations, the measured forces can be associated with a time period. If additional forces are sustained during the time period, the forces are considered cumulative forces. If the forces are sustained outside of the time period, the forces are not considered to be cumulative. In some implementations, the time period can be an hour, several hours, a day, a week, a season, a deployment, or any such time period defined by the user.

For tracking cumulative brain injury, the system 100 is configured to measure forces experienced by the user via sensors 104, 108a-c over time (e.g., seconds, minutes, hours, etc.) and determine an estimate of the cumulative injury to the brain of the user from repeated forces. The system 100 can be configured to assign an identifier to a particular user. When sensor(s) associated with the user measure forces as previously described, the data processing system 102 can determine locations in the brain that experience force loading, as previously described. When additional forces are experienced by the user, the data processing system 102 determines where the additional forces cause force loading in the brain. For estimating (or inferring) injury to the brain (such as a reduction in white matter integrity, as previously described), the data processing system 102 accounts for both the current forces being experienced and prior forces experienced for that user. For example, the data processing system 102 is configured to obtain force data for the user representing a prior amount of force experienced by the user. The data processing system 102 is configured to determine, for the particular location in the brain over a predetermined period of time, a cumulative force loading. The data processing system 102 estimates a cumulative damage estimate by combining the amount of damage of the output data and the prior amount of damage for the user.

As previously described, the data processing system 102 identifies regions of interest of the brain for detecting brain injury. The particular regions are selected based on which regions correspond to brain functionality or integrity that can be adversely affected by force loading of those regions. For example, a midbrain region can be selected based on evidence that reduction of white matter integrity of the midbrain region results in adverse symptoms, and that this can occur in response to force loading of that region. Regions in the brain can be selected for which there is a difference in the force-absorbing ability of the brain such as interfaces between rigid and soft tissues of the brain.

In some implementations, the regions are defined as follows. The data processing system 102 obtains a first mask data representing a defined region of the brain, such as a corticospinal region. The data processing system is configured to obtain second mask data representing a region of interest of the brain (such as a midbrain region). The data processing system 102 is configured to identify voxels or other units representing regions of intersection of the first mask data and the second mask data. The data processing system 102 is configured to define the one or more locations at the regions of intersection. The first mask region can represent any defined region for which Mill feature data are extracted for training the machine learning models or AI models. The second mask data applies to any portion of the brain for which the force loading is being monitored.

Each of the locations or regions of interest in the brain is associated with a weight value of the weight matrix developed for the machine learning model previously described. The data processing system 102 can determine weight values for each region independently from other regions of interest. In some implementations, the weight values for a region depend on physical aspects of the brain for that region. The specific values of the weights are determined by training the machine learning model.

Each region of the brain can be associated with a threshold force loading value that represents a threshold for causing brain damage to that region. In some implementations, the threshold force loading values can each be determined individually based on training of the machine learning model. For example, the threshold of how much force different areas of the brain can be a function of many variables, including for instance the relative elasticities of surrounding tissues for that region. When the force loading for the region exceeds a threshold, the data processing system 102 can generate an alert indicating that a threshold inferred damage level is exceeded, as previously described.

For cumulative damage estimation, the total force loading over a period of time can be considered for inferring damage to the corresponding region. The data processing system 102 is configured to compare the cumulative force loading (e.g., inferred damage estimate) at each location in the brain to a threshold that is specific to that location. The data processing system 102 can generate an alert when the cumulative damage estimate satisfies the threshold, the alert indicating a safety warning.

For cumulative damage estimation, the data processing system 102 is configured to obtain prior damage data representing a prior amount of damage estimated for the particular location in the brain at a first time. The data processing system 102 is configured to obtain time data indicative of a second time associated with the force data. The data processing system 102 is configured to weight the prior amount of damage based on a difference between the first time and the second time. In some implementations, the data processing system 102 is configured to compare estimated damage to a normative measure of structural or functional integrity (e.g., stratified by demographic variables, including age, sex, weight, education, head/neck circumference, BMI, etc) to generate weighted damage data. The data processing system 102 is configured to generate a cumulative damage estimate by combining the weighted damage data and the amount of damage of the output data. In some implementations, weighting the prior amount of damage comprises adjusting an estimated reduction in brain structural or functional integrity as a function of the difference between the first time and the second time (or other later time corresponding to the later measurement of force). In some implementations, the weighting is based on a comparison of the estimated damage to a normative measure of brain structure and function (stratified by demographic variables).

The data processing system 102 thus accounts for two dimensions for generating cumulative inferences. The data processing system 102 generates inferences about cumulative force loading for the locations of the brain. The data processing system 102 generates inferences about cumulative damage to the brain based on that force loading. These two dimensions may not be linearly related. For example, there is a loading force threshold value beyond which damage starts to accumulate at a higher rate. For example, if a user sustains 100 head hits over the course of a few weeks, damage caused by the 100th hit may be far greater than the damage caused by the 10th hit, even though the forces associated with the 100th hit are not greater than (or are even lesser than) the forces associate with the 10th hit. Therefore, the function for estimating cumulative damage based on repeated measurements of forces can be non-linear such that subsequent forces are weighed more heavily than previous forces sustained by the user.

The damage to the brain can be determined based on one or more of a variety of measurable changes to the brain. For example, an amount of damage to the brain can represent a change in the structural integrity of the brain or the functional responsiveness at the particular location relative to an initial or normative value at the particular location. In some implementations, damage to the brain can be represented by a reduction in white matter integrity at one or more locations of the brain. In some implementations, the functional or structural integrity of the brain can be measured by measuring a change in gray matter thickness, change in material properties (e.g. change in stiffness), change in functional connectivity among brain regions, change in functional responsiveness of a brain region measured by functional MIll, MEG, EEG, or fNIRS, a change in peripheral circulatory system levels of brain-based proteins, or a change in signs, symptoms, or other behavioral sequelae of injury (oculomotor dysfunction, loss of consciousness, headache, and so on).

The data processing system 102 is configured to generate data representing the estimated force loadings and/or inferred amount of damage to one or more locations of the brain based on the application of the trained machine learning models or AI models to the sensor data of the sensors 104, 108a-c associated with the user. The output data generated by the data processing system 102 can include data for a visualization of the force loadings to the one or more locations in the brain. For example, the data processing system 102 can generate data for presentation on a screen of the client device 116. The visualization can include heat maps representing force loadings or inferred damage to various locations in the brain that is updated in real-time as additional sensor data are received. The visualization can include tool tips indicating estimated values (either actual or normalized to a scale such as 0-10) of amounts of force or damage on the locations of the brain. The visualization can include indications of whether threshold damage amounts or force loading amounts have been exceeded for any location in the brain of one or more users of the system.

The output data generated by the data processing system 102 can include data other than that in a graphical user interface. For example, the data processing system 102 can generate alerts, tones, push notifications, cause vibrations in a device, or generate any other such data indicative of one or more thresholds being exceeded for a user or a plurality of users in real time or near real time. For example, a belt, watch, necklace, vest, helmet, etc. that is the wearable device can emit a tone indicting to the user of that device that the user has experienced more than permissible amount of force on the brain of the user and warn that the user should cease the activity causing the forces.

The data processing system 102 can be configured to process data for a plurality of instances of the wearable device 106 in parallel. For example, a platoon of soldiers or a team of sports players can be monitored together on a single client device 116. In some implementations, the output data can be multicast to a plurality of client devices over the network 112.

The network 112 can be a wireless network. In some implementations, the network 112 includes a cellular network (e.g., long term evolution (LTE), 5G new radio (NR), etc.). In some implementations, the network 112 includes the internet. In some implementations, the network 112 is a local area network (LAN). In some implementations, the network 112 is a wide area network (WAN). In some implementations, the network 112 is a Bluetooth. Any such network 112 can be used such that data including simple messaging service (SMS), TCP/IP packets, or any such communication protocol is used for transmitting the sensor data and the output data over the network 112.

The data storage 110 can include any device configured for storing electronic data. The data storage 110 can include cloud storage. The data storage 110 can include any kind of database, such as NoSQL databases, columnar databases, wide column databases, object-oriented databases, key-value (relational) databases, hierarchical databases, data lakes, data warehouses, and so forth.

The data storage 110 is configured to store sensor data and output data as needed for operation of the system 100. The data storage 110 can include a plurality of entries for storing data related to different users of the wearable devices 106. For example, the data collected from sensors 104, 108a-c for a particular user can be stored in a record or database entry associated with that user. In some implementations, each time new sensor data are received from the sensors 104, 108a-c, the data are associated with a time stamp indicating a time at which the data were measured. The time stamp data can be used to determine a weighting of the measured force data or whether the force data are applied to a particular period of time for estimating damage to the brain of the user, as previously described.

Figure 2:
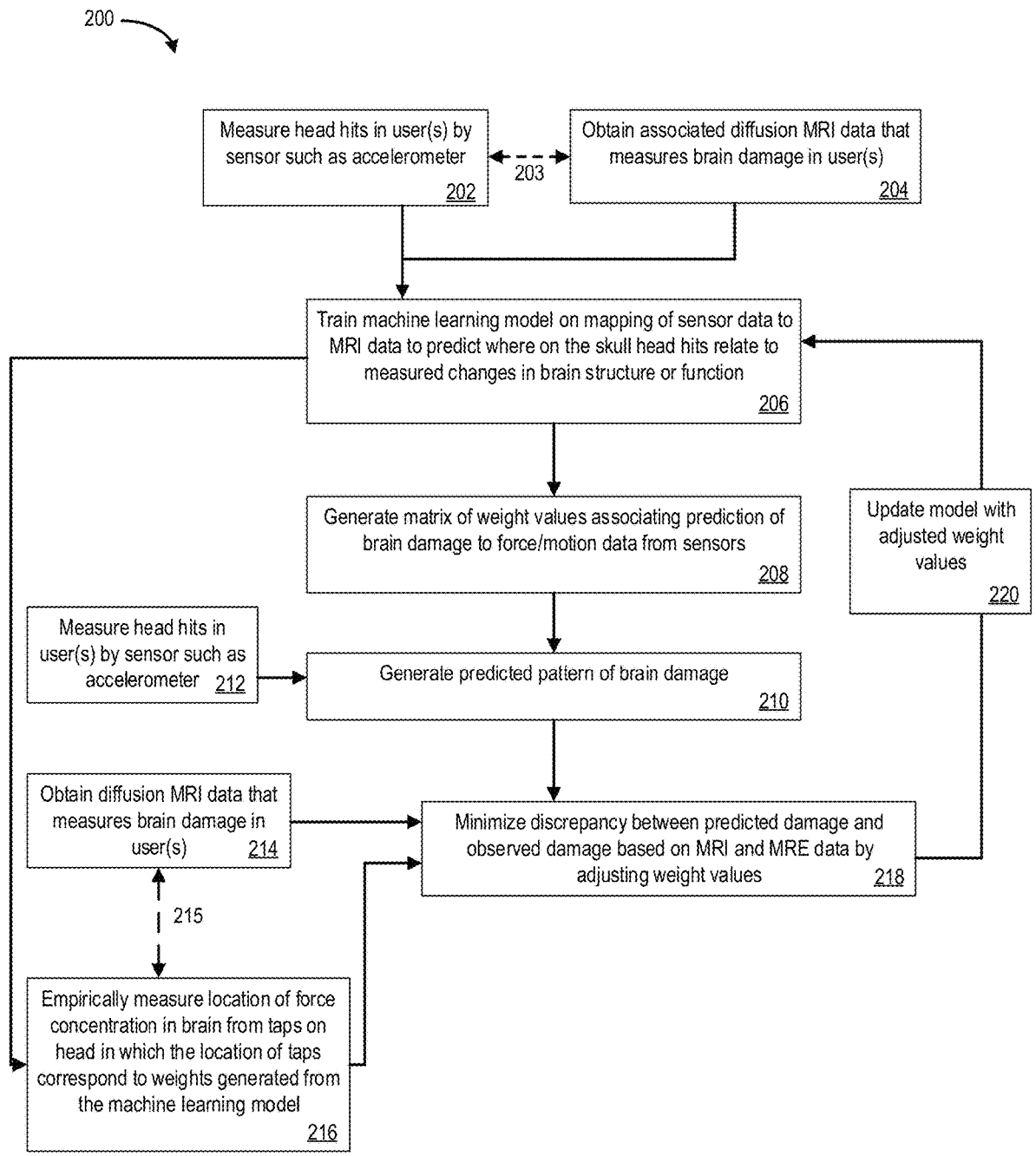
FIG. 2 shows an example process for training a machine learning model.

FIG. 2 shows an example process 200 for training a machine learning model for estimating brain injury from force data measured by force sensors, such as sensors 104, 108a-c. The process 200 can be executed by the data processing system 102. The process 200 can be executed by a data processing system, such as data processing system 102 of FIG. 1, using the sensors 104, 108a-c and wearable devices 106 of FIG. 1.

The data processing system 102 collects training data. This is performed by measuring (202) head hits in user(s) by sensor such as accelerometers or transducers. The data processing system 102 obtains (204) diffusion MM data that measures brain damage in user(s). The motion data or sensor data are associated with the MM data.

The data processing system 102 is configured to map the head hit locations of the sensor data to measured brain damage of the Mill data. The mapping includes training (206) machine learning model on mapping of sensor data to MRI data to predict where on the skull head hits relate to measured changes in brain structure or function. The head hit locations are known based on data fingerprints or data signatures of the sensor data. The MRI data are collected from the users that experienced the forces. There is a known association between these data, shown by the dashed line 203. The data processing system 102 is configured to generate (208) a matrix of weight values associating prediction of brain damage to force/motion data from sensors. As previously discussed, the weight values vary depending on with which region that weighting is associated in the brain. Each location is associated with a weight value.

The data processing system 102 is configured to obtain data representing measured force loading locations for the one or more machine learning predicted locations. The obtained data include measuring (212) head hits in user(s) by sensor such as accelerometer. The machine learning model is configured to generate (210) predicted pattern of brain damage using the weight values that are trained using the MRI data associated with the force data. However, additional MRI data are not needed to generate the estimation-only force data of the sensors.

The trained machine learning model can be refined using MRE data. To refine the machine learning model, the data processing system 102 obtains diffusion MRI data (214) that measures brain damage in user(s). The data processing system 102 obtains data that represents empirically measuring (216) locations of force concentration in brain from taps on head in which the location of taps correspond to weights generated from the machine learning model. These data are associated with the MM data, as shown by arrow 215. The data processing system generates a new prediction based on measured force loading (MRE) data and the MM data. The weight values are adjusted to minimize (218) discrepancy between predicted damage and observed damage. The original machine learning model can be updated (220) with the adjusted weights. Process 200 can be iterated across a dataset using an n-1 data folding approach.

Figure 3:
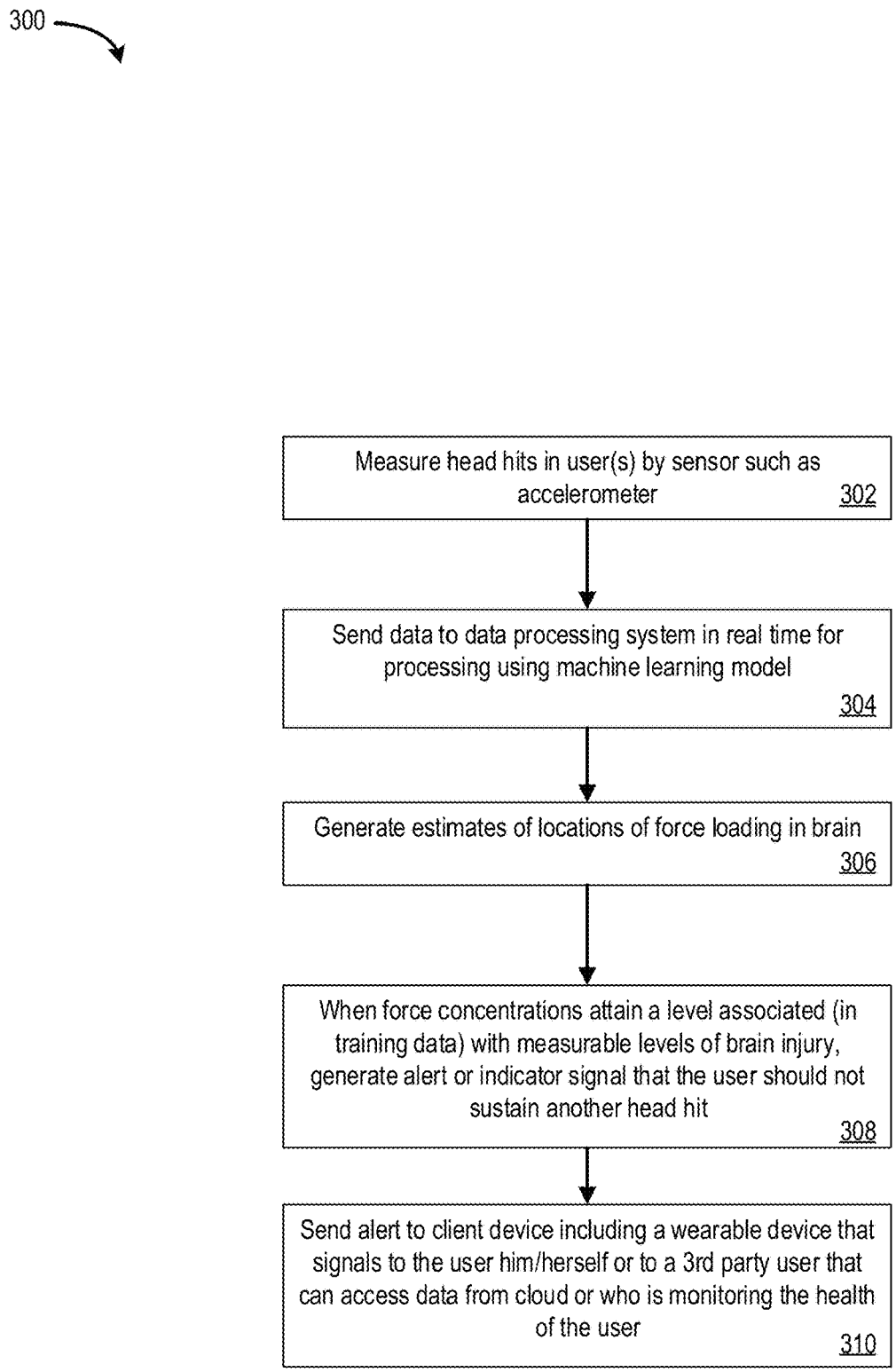
FIG. 3 shows an example process for executing the trained machine learning model, trained by the process of FIG. 2, for real-time determining of brain injury to users.

FIG. 3 shows an example process 300 for applying the trained machine learning model that is trained by the process 200 of FIG. 2. The process 300 can be executed by a data processing system, such as data processing system 102 of FIG. 1, using the sensors 104, 108a-c and wearable devices 106 of FIG. 1. The process 300 includes measuring head hits in user(s) by sensor such as accelerometer. The process 300 includes sending (304) the data to data processing system in real time for processing using machine learning model. The process 300 includes generating (306) estimates of locations of force loading in brain. The process 300 includes generating (308), when force concentrations attain a level associated (in training data) with measurable levels of brain injury, an alert or indicator signal that the user should not sustain another head hit. The process includes sending (310) an alert to client device including a wearable device that signals to the user him/herself or to a 3rd party user that can access data from cloud or who is monitoring the health of the user.

FIGS. 4-10 represent an example implementation of the systems and processes of FIGS. 1-3. The example data presented in FIGS. 4-10 is a non-limiting example of an implementation of the system 100 and processes 200, 300 of FIGS. 1-3.

Figure 4A:
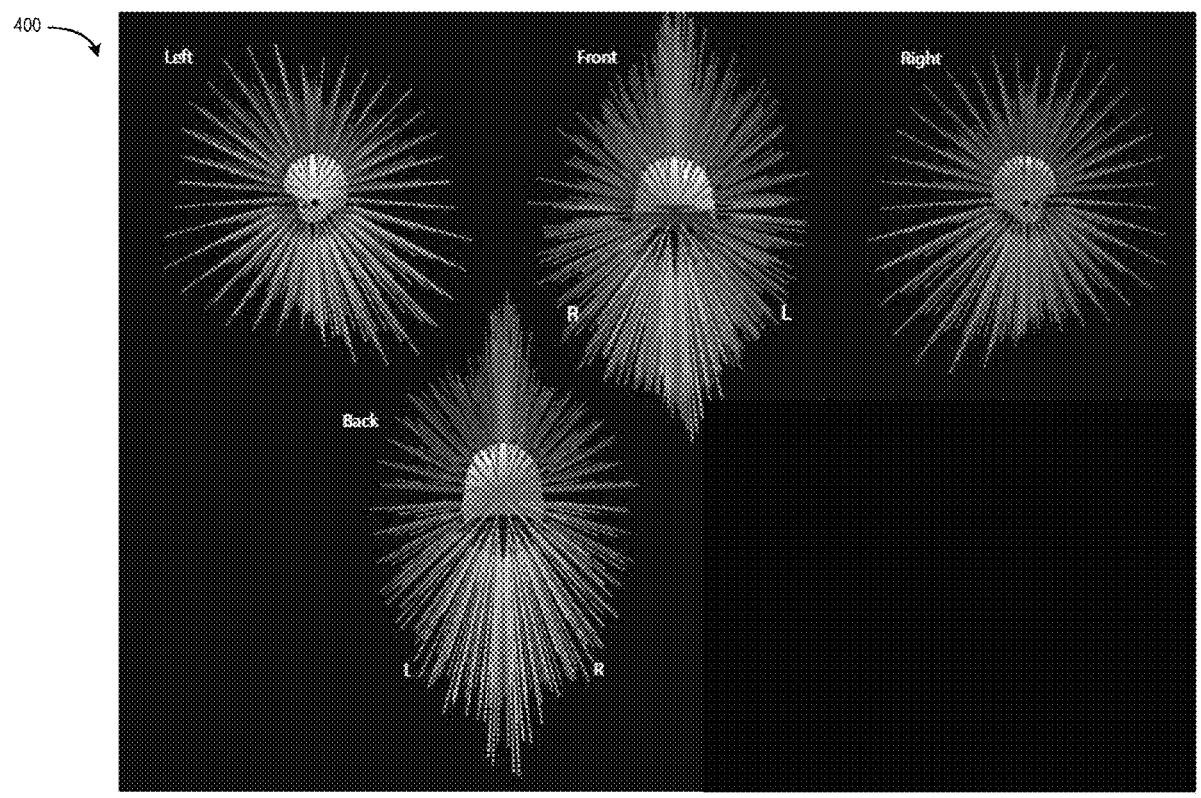
FIG. 4A includes a visualization of spatial distribution of head hits.
Figure 4B:
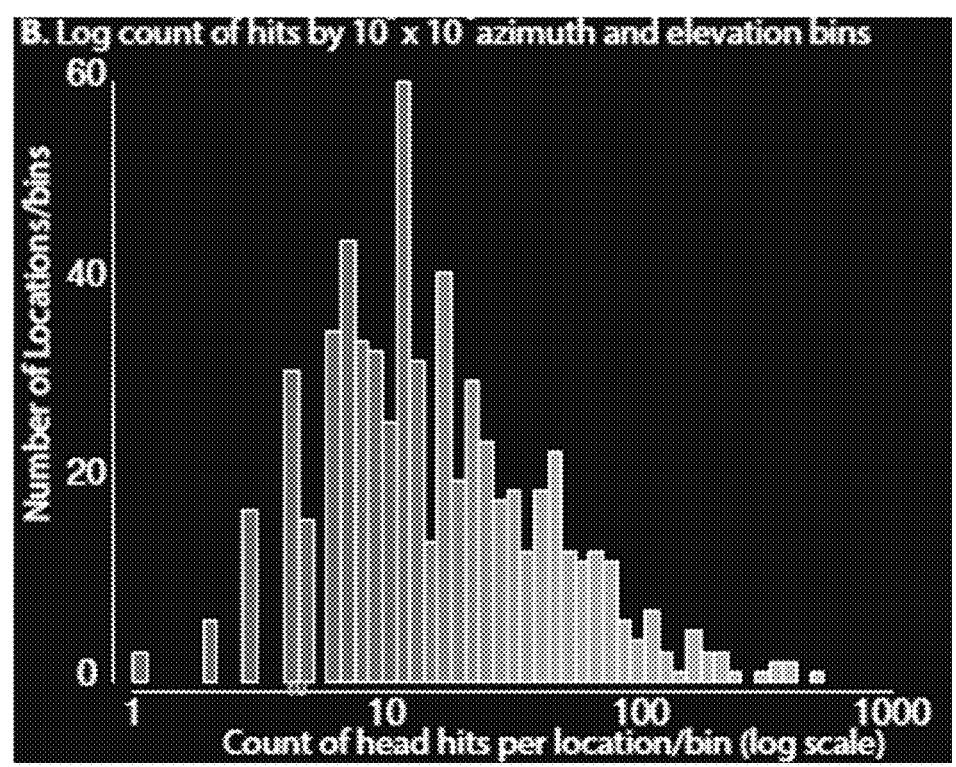
FIGS. 4B-4D show plots of head hits.

FIG. 4A includes a provides a visualization 400 of spatial distribution of head hits in 38 collegiate football players, including a Repetitive Sub-Concussive Head Impacts (RSHI) cohort, for a season of play. FIG. 4B shows plot 410 of log count of hits by location/bin. Azimuth (longitude) and elevation (latitude) of the sensor data were binned into 10° square bins (36 bins for 360 azimuth, 18 bins for 180 degrees elevation). At each location/bin, the total number of hits were counted across all 38 players in the RSHI cohort. Because the distribution of hit count was strongly right skewed (higher counts for a fewer number of hits per location/bin), the $\log_{10}$ of the count data was computed. The results are displayed in visualization 400 as vectors where the color and length of the each vector scales by the log of the count of hits at that location.

FIG. 4B includes a graph 410 that shows a log count of hits by 10°×10° azimuth and elevation bins. The histogram plots (Y axis) the number of locations/bins at which (X axis) different numbers of hits were observed. Shading on the histogram serves as a color scale for the data displayed in visualization 400.

Figure 4C:
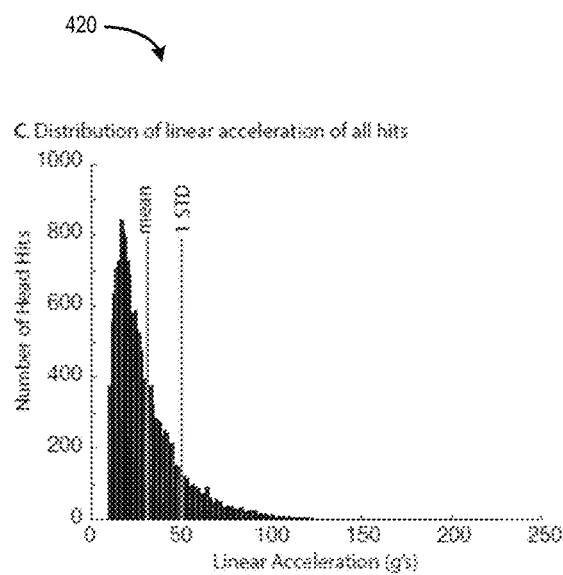
Figure 4D:
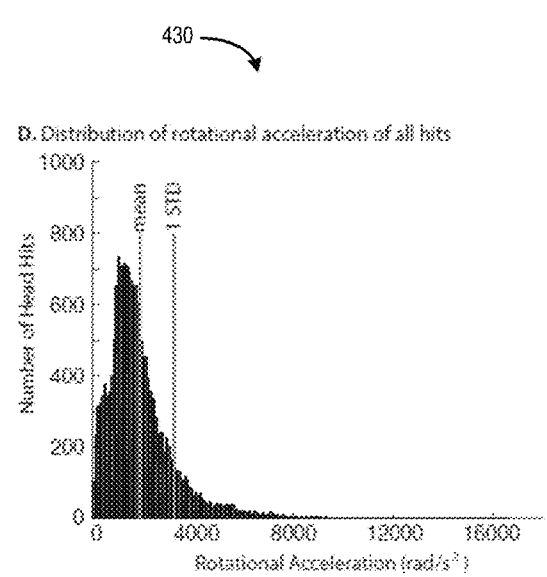

FIG. 4C includes a histogram 420 presenting of distribution of linear acceleration for all hits. FIG. 4D shows a histogram 430 including a distribution of rotational acceleration for all hits of the sensor data.

Figure 5:
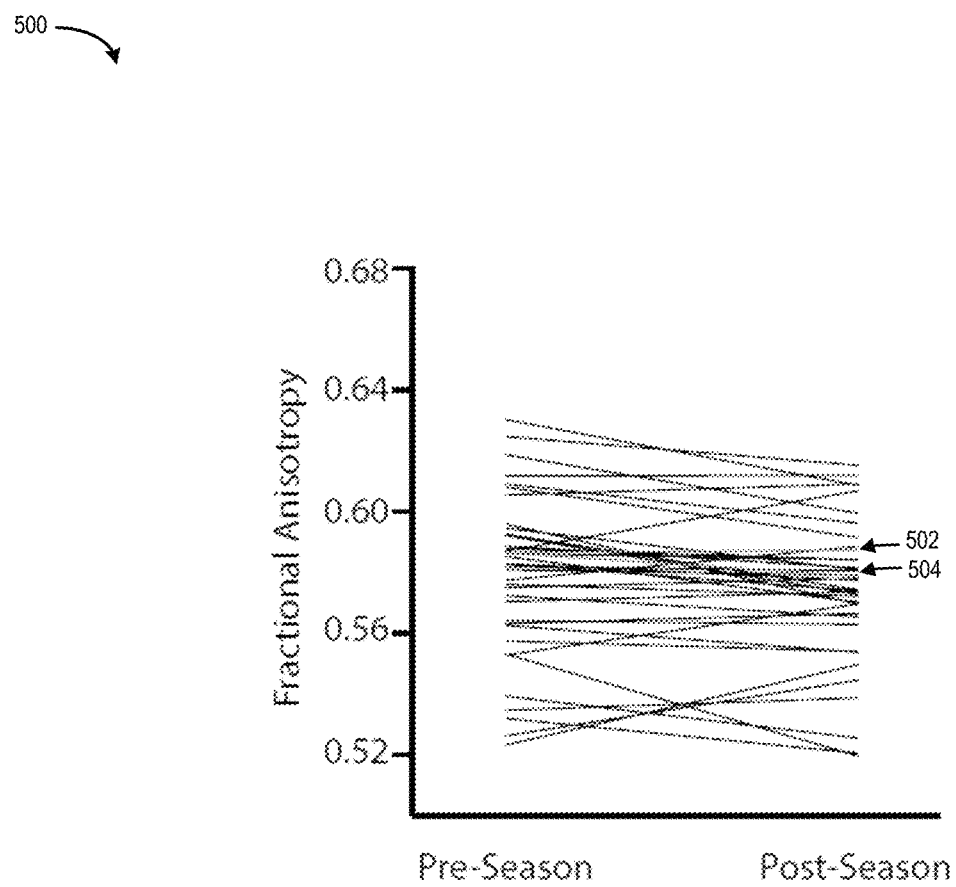
FIG. 5 shows a graph representing white matter integrity for a RSHI cohort.

FIG. 5 shows a graph 500 representing white matter integrity for RSHI cohort. The white matter integrity is reduced post-compared to pre-season in the RSHI cohort. Fractional anisotropy in the right corticospinal tract midbrain ROI was significantly reduced postseason compared to preseason. The light data points/lines 502, 504 correspond to the two players (of the group of 38) who sustained a frank concussion.

Figure 6:
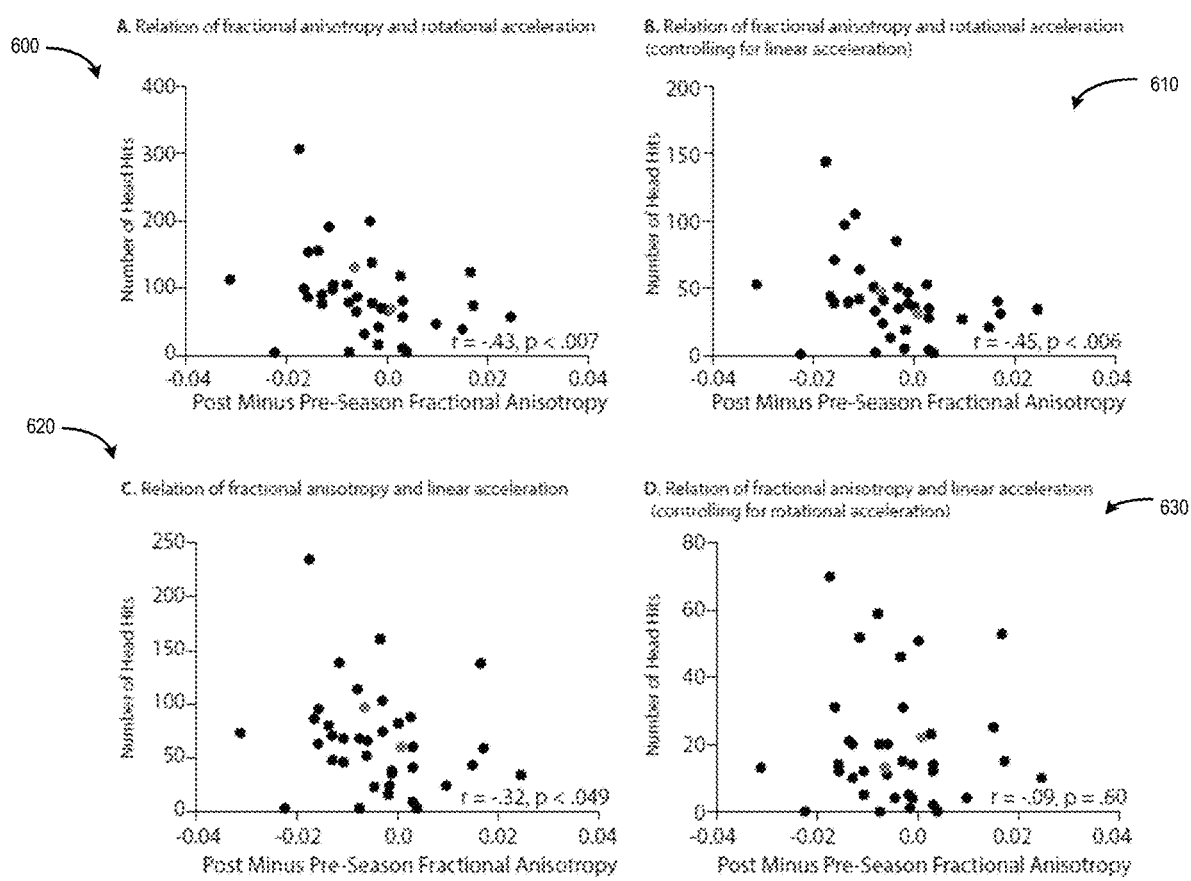
FIG. 6 shows graphs representing correlations between head hits with changes in fractional anisotropy.

FIG. 6 shows graphs 600, 610, 620, and 630 representing correlations between head hits with changes in fractional anisotropy. In all plots, dark circles indicate individuals without clinically diagnosed mTBI. The light circles indicate the two individuals who suffered a concussion between the pre- and post-season MRT. Graph 600 presents a scatter plot showing the relation between changes in fractional anisotropy in the right mid brain and the number of head impacts with rotational acceleration equal to or greater than one standard deviation above the group mean. The direction of the relation indicates that more trauma is associated with greater reductions in structural integrity of white-matter. This relation remained when excluding the two subjects who suffered a clinically defined concussion (r=-0.42, p<0.012). Graph 610 shows the relation between rotational acceleration and changes in fractional anisotropy holds when controlling for linear acceleration, by restricting the analysis to hits that exceed the threshold for rotational acceleration but do not exceed the threshold for linear acceleration. This relation remained when excluding the two subjects who suffered a clinically defined concussion (r=-0.44, p<0.008).

Graph 620 shows the number of head hits with linear acceleration greater than one standard deviation above the mean is negatively correlated with the change (post minus pre-season) in fractional anisotropy in the midbrain. This relation, however, was not significant when excluding the two subjects who suffered a clinically defined concussion (r=0.32, p<0.06).

Graph 630 shows the relation between linear acceleration and changes in fractional anisotropy goes away when controlling for rotational acceleration, by restricting the analysis to hits that exceed the threshold for linear acceleration but do not exceed the threshold for rotational acceleration. This lack of a relation between linear acceleration and changes in DTI remained absent when excluding the two subjects who suffered a clinically defined concussion (r=-0.11, p=0.51).

Figure 7:
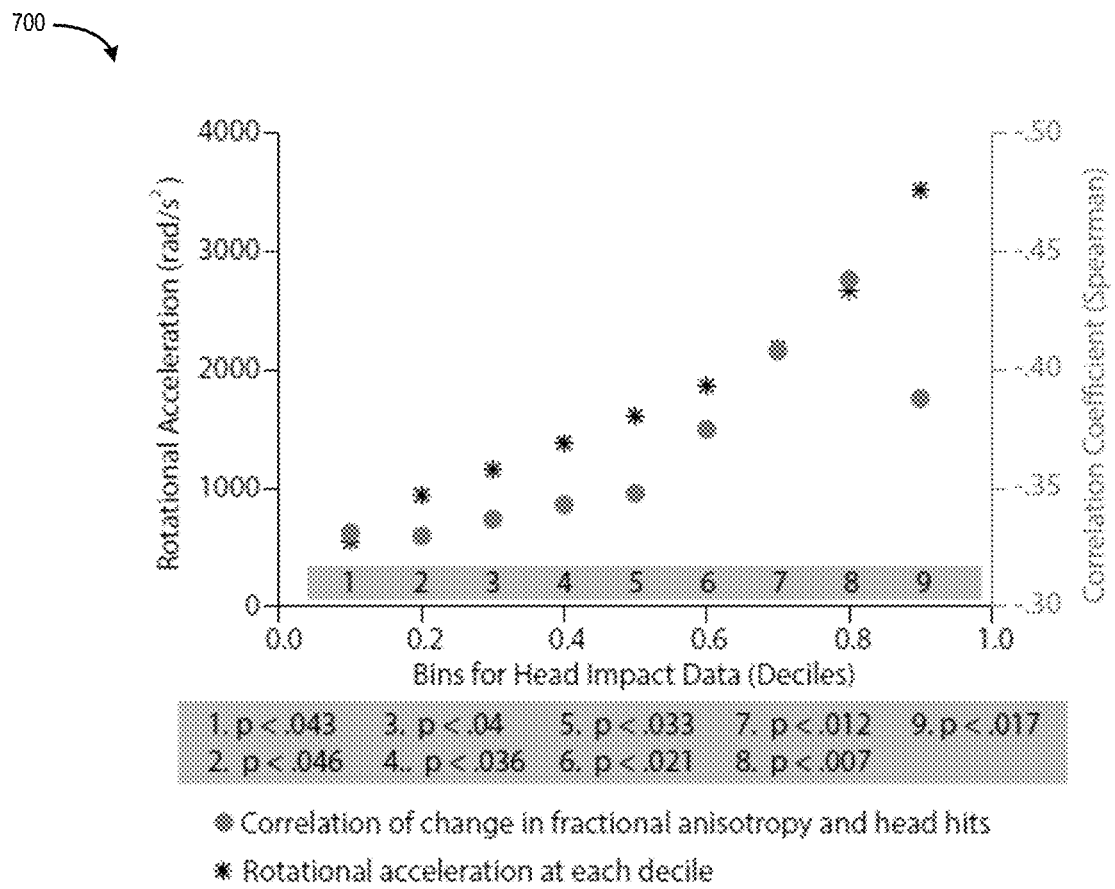
FIG. 7 shows a graph representing control analyses relating sensor data to brain injury.

FIG. 7 shows a graph 700 representing control analyses relating sensor data to brain injury. The graph 700 shows that the relation between rotational acceleration and changes in fractional anisotropy does not depend on thresholds. The plot shows as stars the rotational acceleration values corresponding to decile binning of the data. For each decile, the correlation between the number of hits (at that threshold or higher) and changes in fractional anisotropy was computed (filled red circles). Regardless of the threshold used, there was a significant correlation between changes in fractional anisotropy and number of head hits.

Figure 8:
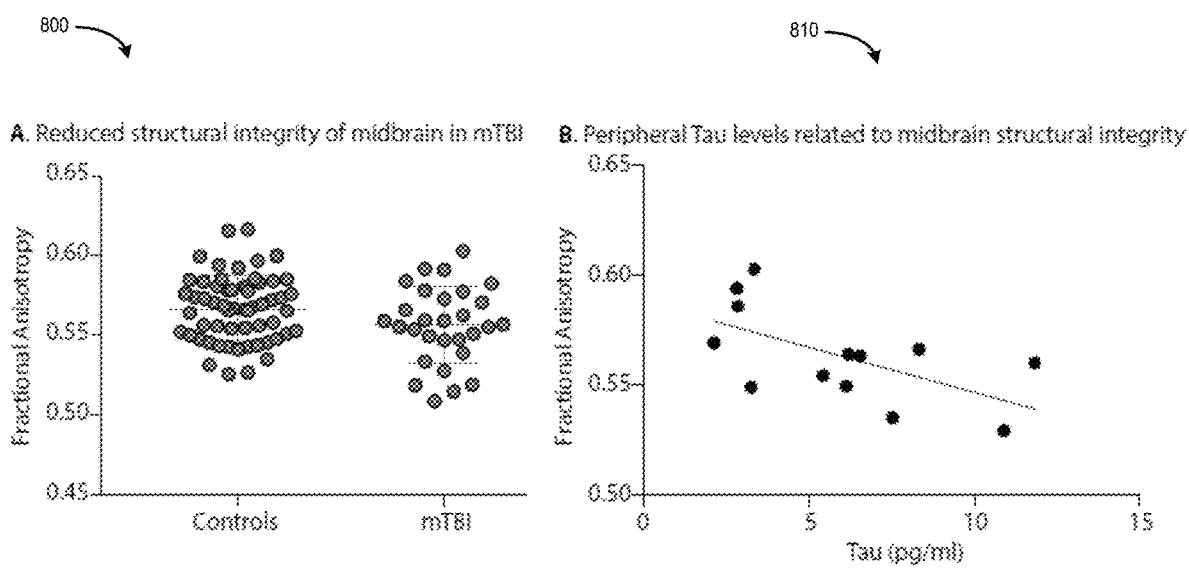
FIG. 8 includes graphs showing white matter structural integrity of the midbrain indexes clinically defined mTBI and relates to peripheral tau.

FIG. 8 include graphs 800, 810 showing white matter structural integrity of the midbrain indexes clinically defined mTBI and relates to peripheral tau. Graph 500 represents ROI analyses of the right corticospinal tract. ROI in the midbrain show significantly reduced fractional anisotropy in individuals diagnosed with a concussion compared to matched controls. Graph 510 shows there is a negative correlation between peripheral tau and structural integrity of the midbrain in concussed individuals, indicating higher levels of peripheral tau are associated with greater reductions in structural integrity of the midbrain corticospinal tracts.

Figure 9A:
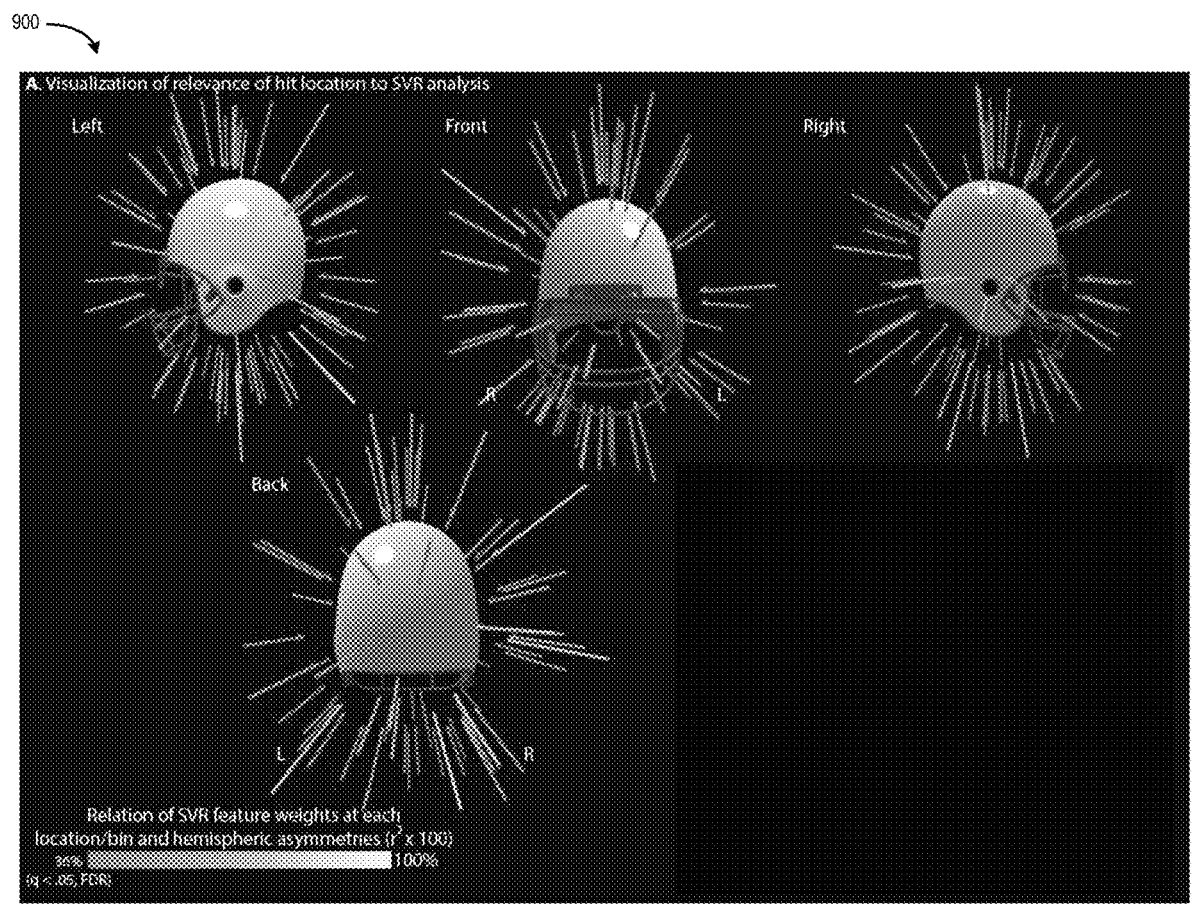
FIG. 9A shows a visualization of a support vector regression (SVR) analysis relating the spatial fingerprint of head impacts to hemispheric asymmetries in white matter.

FIG. 9A shows a visualization 900 of a support vector regression (SVR) analysis relating the spatial fingerprint of head impacts to hemispheric asymmetries in white matter. Each player has a spatial fingerprint of the distribution of hits around the head over the entire season. The fingerprint pattern was used to train a linear SVR model to predict variance across participants in hemispheric asymmetries in white matter changes. Visualization 900 represents a relevance of hit location to SVR analysis. The images are a graphical representation of the SVR model relating variance across subjects in the spatial distribution of hits to variance across subjects in the laterality of white matter changes. This visualization of the SVR analysis was computed by correlating the variance across participants in feature weights (at each location/bin) with the variance across subjects in hemispheric asymmetries in white matter changes. The results are plotted as vectors that are scaled in length and color by variance explained (e.g., a Bonferoni threshold is applied at 05/648=0.00007, or a critical r2 of 0.36).

Figure 9B:
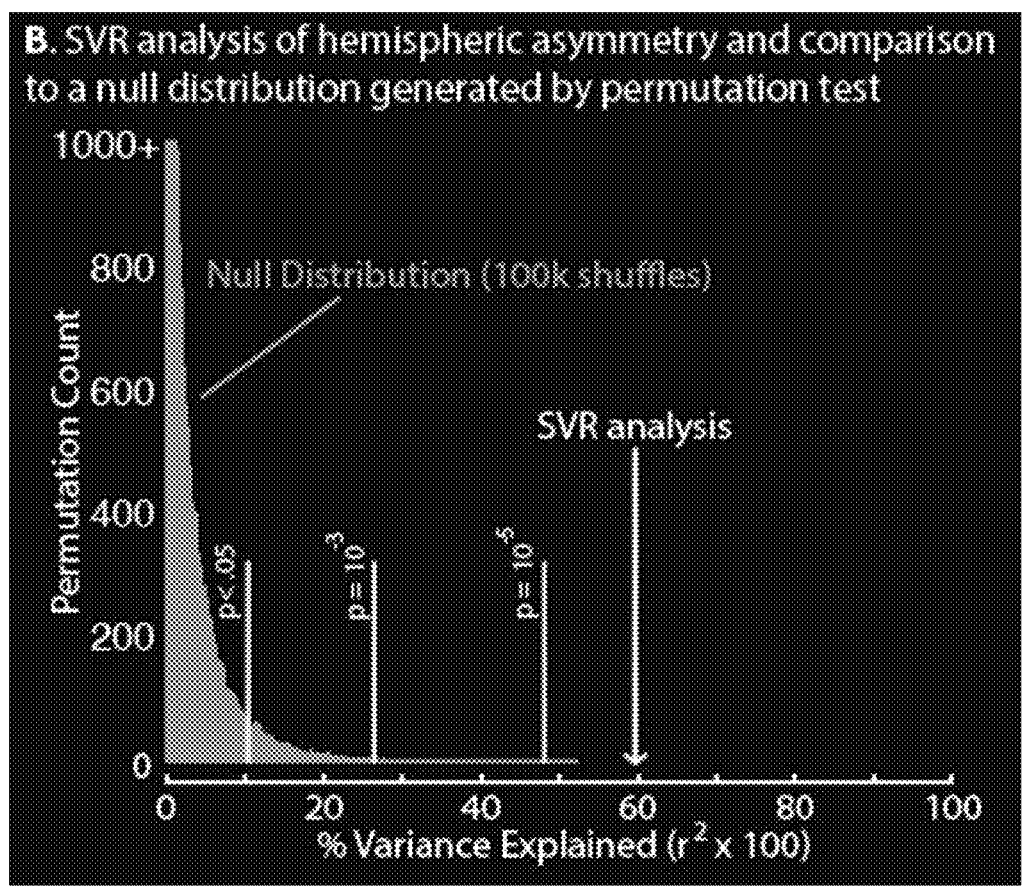
FIG. 9B show a graph of an SVR analysis of hemispheric asymmetry and comparison.

Graph 910 of FIG. 9B presents an SVR analysis of hemispheric asymmetry and comparison. Using an n−1 cross-validation approach, a linear SVR model captures 60% of the variance in hemispheric asymmetries in white matter changes. The variance explained by this analysis differs significantly. from chance, as shown through permutation testing (e.g., by 100,000 shuffles).

Figure 10:
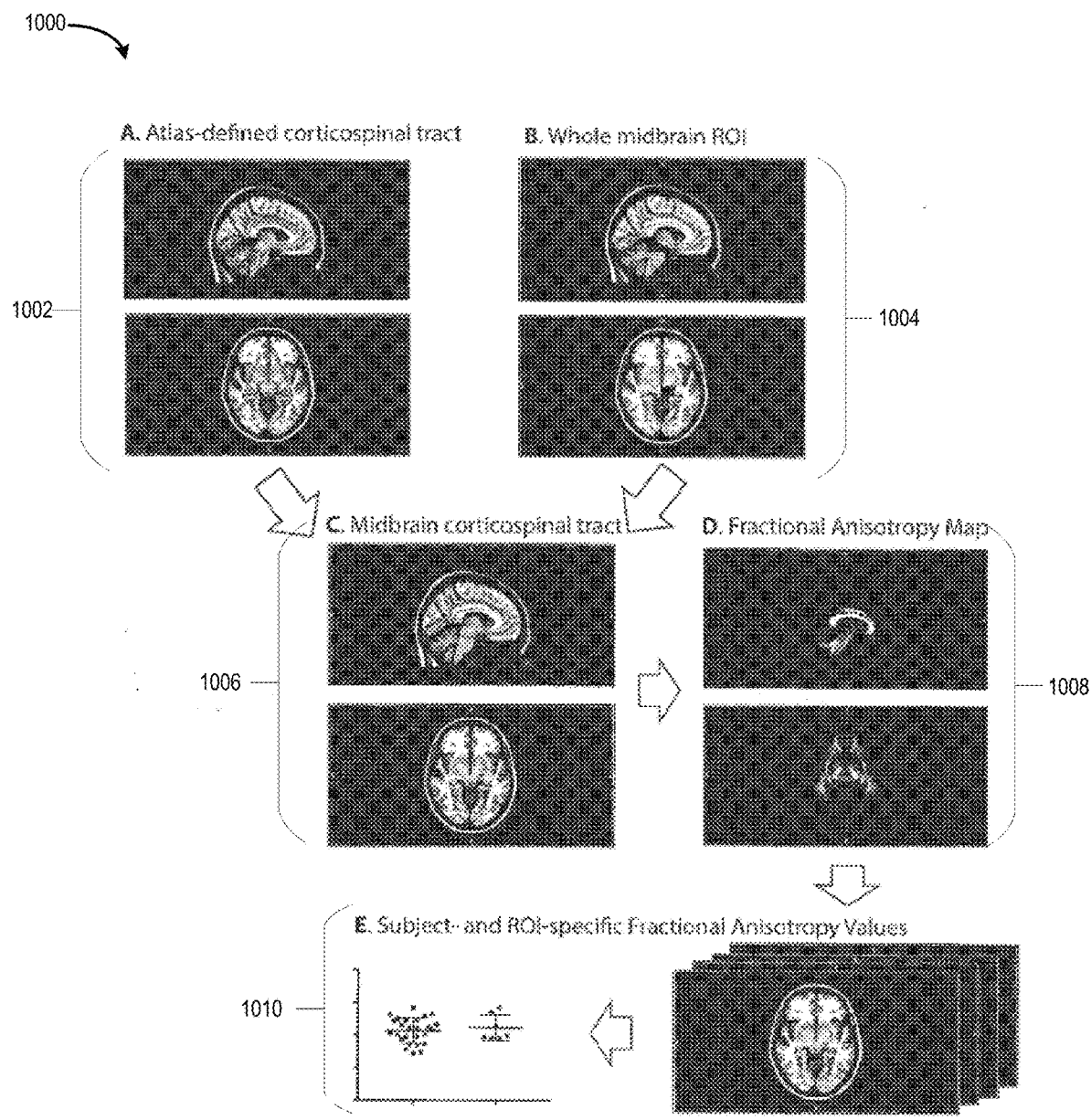
FIG. 10 presents a process 1000 of how fractional anisotropy values were extracted for the corticospinal tract (CST) ROI in the midbrain Like reference symbols in the various drawings indicate like elements.

FIG. 10 presents a process 1000 of how fractional anisotropy values were extracted for the corticospinal tract (CST) ROI in the midbrain. An intersection was computed between the atlas defined corticospinal tract (1002) and a midbrain ROI (1004). The resulting midbrain ROI for the corticospinal tract (1006) was used to extract fractional anisotropy values from each subject's whole-brain global fractional anisotropy map (1008), and the results averaged over all voxels in the ROI and plotted (1010).

The midbrain is a key structure that can serve as an index of injury in both clinically-defined concussions, and repetitive sub-concussive bead impacts. The midbrain is biomechanically susceptible to the rotational loading of head impacts and mTBI. The midbrain is implicated in neurodegeneration (e.g., chronic traumatic encephalopathy, or CTE) in people such as football players and military servicemen. Generally, the midbrain is clinically relevant for functions such as oculomotor control and auditory processing which are often impaired in mTBI.

MRI-based measures of white matter integrity in the mid brain were examined for developing a succinct index of repetitive head injury. Relevant MRI-based measures of midbrain structural integrity can serve as a biomarker of repetitive head hits. Furthermore, the temporal fingerprint of force loadings that athletes' brains sustain (as measured with helmet worn accelerometers, such as sensors 104, 108a-c of FIG. 1) relates to MRI-based measures of midbrain structural integrity.

MRI-based measures of midbrain white-matter integrity provided a neural sequela of sub-concussive brain injury across three age brackets and levels of football athletes (e.g., high school, collegiate, and professional). The data acquired was used to develop a wearable device, such as wearable device 106a-b of FIG. 1, which utilizes machine learning algorithms and accelerometers to provide real-time feedback on return-to-play decisions.

The system 100 developed from the experimental data generated herein provides predictions about the risk that additional head hits have for long-term health of neurological structures. In order to develop those methods, machine-learning algorithms and software are developed and refined machine-learning algorithms and software that provide feedback about that risk profile. The relationship between the temporal fingerprint of sub-concussive rotational loading and MMI-based measures of midbrain structural integrity is mapped using the machine learning models or AI models described herein.

Spatio-temporal fingerprints of head trauma that predict changes in brain structure and function are collected and identified. Generally, CTE is related to cumulative sub-concussive head hits, rather than clinically defined concussive hits (e.g., mTBI). Sub-concussive force loading on the central nervous system is a silent injury that the system 100 is configured to detect. The system 100 is configured to quantify neurologic injury associated with sub-concussive head hits and translate those measures into actionable information that be used in real-time to protect players of contact sports or combat soldiers exposed to explosive shock waves.

For collecting the experimental data described herein, cohorts of athletes are followed with helmet-worn accelerometers for practice and play, and pre-season and post-season diffusion tensor MM and oculomotor tests are conducted. A relation between the cumulative rotational loading sustained by players' brains (e.g., measured with sensors such as accelerometers) and each of reductions in structural integrity of midbrain structures, and fine-grained measures of oculomotor function (e.g., eye movements) were determined. Athletes at different stages of their careers are tested to analyze changes in the resiliency of the brain from the mid-teen years through the 20s and early 30s (as in professional athletes), and measure cumulative effects on core outcome measures of number of years spent playing football.

Generally, repetitive head hits in the absence of clinically defined concussion are associated with a decrease in white matter integrity in the mid brain. Additionally, a spatio-temporal fingerprint of sub-concussive rotational loading (measured with helmet-worn accelerometers) predicts MRI-based measures of structural integrity in the midbrain.

The midbrain provides a reliable and sufficient index of clinically silent neuro trauma. Each athlete enrolled in the study was tested twice. Each athlete completed a MM, and psychometric testing at each visit. Psychometric testing included but was not limited to an ImPACT test, measures of smooth pursuit and saccadic eye-movements, and basic visual and auditory sensitivity testing.

The MM diffusion data was preprocessed by correcting for magnetic susceptibility distortions, motion and eddy currents. Each participant's diffusion-weighted image and field map magnitude image was stripped of skull artifacts. Gaussian smoothing is applied using σ=4 mm. The magnitude image is warped based on this smoothing, with y as the warp direction, Eddy current correction was performed by taking a volume of each diffusion-weighted image and registering the volume to a Bo image to correct for both eddy currents and motion. The deformed magnitude image was registered. The resulting transformation matrix is then applied to the prepared field map. Distortions are removed from the diffusion-weighted image using the registered field map. Intensity correction is applied to this unwarping. Upon completion of preprocessing, the diffusion tensors are reconstructed. A linear regression to fit a diffusion tensor model at each voxel of the preprocessed diffusion image was used to generate fractional anisotropy (FA), mean diffusivity (MD), radial diffusivity (RD) and axial diffusivity (AD) maps for each subject. This approach represents one example process of how diffusion-weighted images can be processed but analysis of diffusion data is not limited to those specific steps.

To isolate the midbrain region of the corticospinal tract a whole brain image containing a mask of the entire midbrain was multiplied with an atlas-defined mask of the corticospinal tract (CST), separately for the left and right hemispheres. The midbrain region is obtained using a standard space atlas, and the corticospinal tract map is obtained from an atlas of white matter regions in standard space. Voxels are identified that represent the intersection of those two images, which results in an objective (e.g., automated) definition of the CST in the midbrain. The resulting CST ROI for each subject is used to extract the average fractional anisotropy values from the fractional anisotropy map in standard (MNI) space. A schematic illustration of these steps is represented in FIG. 10. The process 1000 of defining midbrain ROIs does not require band-drawn RCHs and is thus an objective means to defining the key regions to ensure generalizability and replicability.

In the experiment now described, a total of 19,128 head impacts (hits) are sustained across 38 players. Of all the hits, 59% (11,334) are sustained in practice, and 37% (7,022) in competition. The remaining 4% of the hits where sustained in other settings such as scrimmages and meetings. In games, players sustained hits with a median rotational acceleration of 1631.7 rad/s2 (mean=1947.5 rad/s2). A median rotational acceleration for hits sustained during practice was 1585.5 rad/s2 (mean=1817.5 rad/s2). For linear acceleration, a similar pattern was observed with numerically higher median and mean linear acceleration during games (median=25.1 g, mean=31.52 g) than during practice (median=24.9 g, mean=30.1 g).

To determine that reduced structural integrity of midbrain white matter is related to head hits, rather than nonspecific variables associated with playing football, a relation between the amount of structural degradation in the midbrain and the amount of head trauma each player sustained is shown. To test for a link between changes in midbrain structural integrity and head-hits,) head hits, as measured by the helmet worn accelerometers, are correlated with changes in fractional anisotropy (post-season minus pre-season), across the cohort (n=38). To determine thresholds of the force parameters in an objective manner, a number of impacts with rotational acceleration or linear acceleration one standard deviation (SD) above the mean for each type of inertial loading was used, calculated across the cohort. Those thresholds corresponded to a linear acceleration of 50.7 g and rotational acceleration of 2,782 rad/s$^2$. The number of impacts with supra-threshold rotational acceleration was inversely correlated with changes in fractional anisotropy (r=−0.43; p<0.008), as shown in FIG. 5. The number of impacts with supra-threshold linear acceleration are marginally correlated with changes in fractional anisotropy (r=−0.32; p<0.049), as shown in FIG. 5. After two subjects in the RSFU cohort who sustained a clinically diagnosed mTBI during the season are removed, the relationship still held. There was an inverse relation between rotational acceleration and changes in midbrain fractional anisotropy (r=−0.42; p<0.01), but only a marginal relation for linear acceleration (r=−0.32; p<0.06).

To assess the independent effects of rotational and linear acceleration a number of impacts are analyzed that met the threshold for one type of acceleration but not the other. The number of impacts with rotational acceleration greater than 2782 rad/s$^2$ and linear acceleration less than 50 g are inversely correlated with changes in fractional anisotropy (r=−0.45; p<0.006). However, hits with linear acceleration greater than 50 g and radial acceleration less than 2782 rad/s$^2$ are unrelated to changes in fractional anisotropy (r=−0.09; p=0.60). These patterns remained when excluding the two players who suffered clinically defined concussion.

The machine learning model was developed using the spatio-temporal fingerprint of sub-concussive rotational loading. Time-lags between successive head hits relate to the cumulative effects on brain structure and function are determined. The system 100 is configured to generate estimates or inferences that are directly relevant to the most urgent decisions that must be made on the field, which are whether athletes are safe to return to play, or whether soldiers are fit to return to the battlefield.

To relate the spatial pattern of hits across the head to hemispheric asymmetries in white matter damage, the following approaches are taken. A used SVR was used to test for a relation between the spatial pattern of hits across the head and hemispheric asymmetries in white matter changes. This analysis was carried out over the RSHI cohort (n=38), as that was the cohort for which we had accelerometer data. A laterality index was calculated for each participant ((RightPost-Season-RightPre-Season) . . . (LeftPost-Season-LeftPre-Season))/(RightPost-Season-RightPre-Season+ LeftPost-Season-LeftPre-Season). The laterality index scales between −1 and 1 and represents the (Y) values to be predicted in the SVR model. The accelerometer output includes, for each registered hit, the azimuth (360 degrees, longitude) and elevation (180 degrees, latitude) of the impact. 0° azimuth is referenced to the back of the head, +90° to the right side of the head, −90° to the left side of the head; −90° elevation is pointing to the ground; +90° elevation is pointing up. A three-dimensional histogram of the cumulative number of hits in equally spaced 10° bins of azimuth and elevation was calculated for each participant (36 bins for azimuth; 18 bins for elevation). The 648 locations or bins containing the total number of impacts sustained for each player is the spatial fingerprint of hits for that player. Those data are converted to a vector (length=648) and normalized to have sum=1 for all players.

SVR was carried out using a linear kernel and with 20 support vectors, using 38 folds. On each data-fold, the SVR model was trained to map laterality indices to the spatial fingerprints for n−1 subjects. The model was then tested by providing the nth subject's spatial fingerprint or feature vector and having the model generate or predict the laterality index. The squared correlation coefficient, between the model-based predicted and the observed laterality indices, was tested for significance in two v<lays. First, it lwas compared to the standard distribution (e.g., the critical r$^2$ for 37 degrees of freedom for an alpha of 0.01 is 0.17). 100,000 permutation tests are performed. For each permutation, laterality indices and feature vectors are randomly shuffled, and then 38-fold cross validation was carried out. The r$^2$ between SVR-predicted laterality indices and the ground truth was calculated for each permutation test, and the results plotted as the null distribution, as shown in graph 910 of FIG. 9.

In order to visualize the results of the SVR analyses, feature weights from the SVR model for each azimuth-elevation bin are correlated across subjects with observed laterality indices. The results as shown in graph 900 of FIG. 9A as vectors at each location/bin of azimuth and elevation. Generally, SVR can be replaced by other ML or AI approaches, or hybrid AI/ML approaches, thus the process is not limited to the use of SVR (here or elsewhere).

Venous blood was collected in a non-fasting state in lavender top EDTA tubes and placed on ice until processed. All blood was centrifuged less than 60 minutes from the time of blood draw, at 4° C. at 3,000 rpm for 10 minutes. Plasma was isolated and samples are stored in a −80° C. freezer until batch assayed, blinded to all other study measures. Analyses are carried out using a proprietary single-molecule sensitive technology. Plasma levels of Tau are measured using a single molecule enzyme-linked immune-array. A combination of monoclonal antibodies was used, where a subset of those antibodies detects tau by targeting the mid-region, while another subset is used for detection against the N-terminus. This process provides molecular level sensitivity while minimizing sample use and error levels.

MRI-based measures of midbrain white matter integrity at the level of the corticospinal tracts in collegiate football players is decreased after a season of play compared to pre-season measures. There is a reduction in fractional anisotropy of right midbrain structures in collegiate football players at their postseason assessment compared to their preseason assessment. The degree of reduction in structural integrity to midbrain structures is correlated with the number of head hits the players sustained, shown in FIG. 6.

Reductions in midbrain white-matter integrity are related to the amount of rotational (but not linear) acceleration that players' brains sustain. Rotational acceleration is the primary driver of changes in white matter structural integrity of the midbrain. As shown in FIG. 7, there is a significant relation between the accelerometer-based measures of rotational loading and changes in fractional anisotropy, across a broad range of thresholds on the accelerometer data. A reduced midbrain structural integrity in an mTBI cohort exists when compared to age- and sex-matched controls, as shown in graph 800 of FIG. 8. Levels of peripheral tau are correlated with MM-based measures of midbrain white-matter structural integrity, as shown in graph 810 of FIG. 8. These analyses reinforce the core inference that white-matter integrity in the midbrain indexes neuro-trauma is common to sub-concussive repetitive head hits and clinically defined concussion or mTBI.

White matter changes are differentially expressed in the right hemisphere. Graph 910 of FIG. 9B shows the results of a linear multivariate analysis (SVR) using an n−1 cross validation approach. There is a relation between the pattern of hits across the head and hemispheric asymmetries in white matter changes (r2=0.595, p<0.0001). Graph 910 also plots a null distribution generated by a permutation tests of the same analysis performed over randomly shuffled data (100,000 shuffles) and indicates that the SVR-based prediction on unshuffled data is significantly different from the null distribution.

To visualize this analysis, the correlated variance across subjects in SVR feature weights, at each location on the head, with variance in the laterality index, across players, is plotted in image 900 of FIG. 9A. Comparing image 900 to image 400 of FIG. 4A, which plots the distribution all hits across the head, shows a sparseness in terms of the locations on the head where variance in SVR feature weights relate to variance in hemispheric asymmetries in white matter changes.

While this specification includes many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

What is claimed is:

1. A system for detecting an injury to a brain, the injury being caused by a force applied to a portion of a user, the system comprising:

at least one sensor configured to output force data specifying the force applied to a portion of the user;

at least one processing device configured for communication with the at least one sensor; and a memory storing instructions that, when executed by the at least one processing device, cause the at least one processing device to perform operations comprising:

receiving the force data from the sensor, the force data including values of force that include at least one value indicating an amount of the force applied to the portion of the user and at least one value indicating a direction of the force applied to the portion of the user;

accessing a machine learning model configured to generate mapping data specifying a weighting for at least one relation between the values of force and values of magnetic resonance imaging (MRI) data that specify changes in a functional responsiveness, functional or structural integrity, or both the functional responsiveness and the functional or structural integrity of the brain at one or more locations in the brain, the values of force associated with the one or more locations and representing a force distribution across the brain;

estimating, based on the mapping data and the force data, an amount of force loading at one or more particular locations in the brain based on the force distribution across the brain represented by the values of force; and generating, based on the estimating, output data representing an amount of damage to the brain at the one or more particular locations in the brain.

2. The system of claim 1, the operations further comprising:
obtaining prior damage data representing a prior amount of damage estimated for the one or more particular locations in the brain over a predetermined period of time;
generating a cumulative damage estimate by combining the amount of damage of the output data and the prior amount of damage;
comparing the cumulative damage estimate at each location in the brain to a threshold that is specific to that location; and
generating an alert when the cumulative damage estimate satisfies the threshold or is projected to satisfy the threshold, the alert indicating a safety warning.

3. The system of claim 1, wherein the amount of damage to the brain represents a change in the structural or functional integrity of the brain or the functional responsiveness at the particular location relative to an initial or normative white matter integrity value at the particular location.

4. The system of claim 1, wherein the at least one value indicating the direction of the force applied to the portion of the user comprises an azimuth value, elevation value, or combination of the azimuth value and elevation value.

5. The system of claim 1, the operations further comprising:
obtaining prior damage data representing a prior amount of damage estimated for the one or more particular locations in the brain at a first time;
obtaining time data indicative of a second time associated with the force data;
weighting the prior amount of damage based on a difference between the first time and the second time or weighting the prior amount of damage based on a comparison of the values of the MRI data to normative data representing a normative measure of structural or functional integrity of the brain;
generating, based on weighting the prior amount of damage, weighted damage data; and
generating a cumulative damage estimate by combining the weighted damage data and the amount of damage of the output data.

6. The system of claim 5, wherein weighting the prior amount of damage comprises adjusting a value representing an estimated reduction in brain structural, material, or functional integrity, the value being adjusted as a function of the difference between the first time and the second time, or the value being adjusted based on the comparison of the values of magnetic resonance imaging (MRI) data to the normative data representing the normative measure of structural or functional integrity of the brain, the normative data being stratified by one or more demographic parameters describing the user.

7. The system of claim 1, wherein the machine learning model comprises a plurality of weight values, wherein one or more weight values of the plurality of weight values correspond to the one or more locations in the brain, and wherein a given mapping between a given value of force of the values of force and a given change in the structural integrity or the functional responsiveness of the brain is based on at least one weight value of the plurality of weight values.

8. The system of claim 7, wherein the machine learning model is trained using associations between the magnetic resonance imaging (MRI) data and fingerprints of the force data, the MRI data representing values for one or more features of the brain, and the fingerprints of the force data representing values for one or more features of rotational force, translational force, or a combination of rotational and translational forces.

9. The system of claim 8, wherein the values of the one or more features of the brain are based on a diffusion tensor or fiber orientation distribution model, a measure of grey matter thickness, or a measure of non-directional diffusion properties including mean diffusivity, applied to voxels of the MRI data, and wherein the features comprise one or more of a fractional anisotropy (FA) map, a mean diffusivity (MD) map, a radial diffusivity (RD) map, an axial diffusivity (AD) map or an apparent fiber density (AFD) map.

10. The system of claim 7, wherein the machine learning model is trained by performing operations comprising:
receiving data, from Magnetic Resonance Elastography (MRE), a slip interface imaging (SII), or a combination thereof, representing a measurement of a location of a force concentration due to inherent material property characteristics of a region in the brain or boundary conditions between this region and its adjacent structures in the brain that is mapped to a location of the force on the portion of the user; and
minimizing, based on the MRE data, a difference between a predicted damage to the brain based on the machine learning model and a measured damage to the brain from the MRI data, the minimizing comprising updating one or more weight values of the plurality of weight values.

11. The system of claim 1, wherein the one or more locations are defined by performing operations comprising:
obtaining first mask data representing a defined region of the brain:
obtaining second mask data representing a midbrain region of interest;
identifying voxels representing regions of intersection of the first mask data and the second mask data; and
defining the one or more locations in the brain as being the regions of intersection.

12. The system of claim 1, further comprising a hardware indicator, wherein the operations further comprise:
causing the hardware indicator to activate in response to generating the output data.

13. The system of claim 1, wherein the at least one sensor comprises one of a transducer or an accelerometer.

14. The system of claim 1, wherein the force data comprises a representation of rotational force sustained by the brain, a representation of translational force sustained by the brain, or a combination of the translational force and the rotational force.

15. The system of claim 1, wherein the at least one sensor is coupled to a wearable device configured to be worn by the user.

16. The system of claim 1, wherein the force data represents a sub-concussive impact or an asymptomatic impact to the portion of the user as well as symptomatic impact or concussive impact to the portion of the user.

17. The system of claim 1, wherein the at least one processing device is part of a cloud computing platform.

18. The system of claim 1, wherein the amount of damage to the brain represents an estimate of a breakdown in a blood-brain barrier of the brain.

19. The system of claim 1, wherein generating the output data representing the amount of the damage to the brain at the one or more particular locations in the brain comprises transmitting the output data to a remote device.

20. The system of claim 1, wherein the operations comprise generating the output data representing the amount of the damage to the brain at the one or more particular locations in the brain in real-time or near real-time.

21. The system of claim 1, wherein the force data represents a physical hit on the portion of the user, a whiplash from a body hit, a blast force applied to the portion of the user, or a combination of the physical hits and the blast force.

22. The system of claim 1, the operations further comprising validating the output data using a rheological process based on receiving data representing an analysis of cadaveric brain materials or three-dimensional printed non-biological material.

23. The system of claim 1, the operations further comprising:
generating a prediction of an amount of time for the user to rest before further exposure to forces.

24. The system of claim 1, wherein the one or more locations in the brain comprise locations of tissue interfaces or vascular interfaces or both in the brain.

25. A system for detecting an injury to a brain, the injury being caused by a force applied to a portion of a user, the system comprising:
at least one processing device configured for communication with a data source, the data source providing Magnetic Resonance Elastography (MRE) data representing a measurement of a location of a force concentration in the brain of the user due to inherent material property characteristics of a region in the brain or boundary conditions between the region and adjacent structures in the brain; and
a memory storing instructions that, when executed by the at least one processing device, cause the at least one processing device to perform operations comprising:
receiving the MRE data, the MRE data representing the measurement of the location of the force concentration in the brain;
accessing a machine learning model configured to generate mapping data specifying at least one relation between values of the measurement of the location of the force concentration in the brain and changes in a functional responsiveness, functional or structural integrity, or both the functional responsiveness and the functional or structural integrity of the brain at one or more locations in the brain;
estimating, based on the mapping data, an amount of force loading at one or more particular locations in the brain of the one or more locations in the brain; and
generating, based on the estimating, output data representing an amount of the damage to the brain at the one or more particular locations in the brain.

26. The system of claim 25, the operations further comprising:
obtaining prior damage data representing a prior amount of damage estimated for the one or more particular locations in the brain over a predetermined period of time;
generating a cumulative damage estimate by combining the amount of damage of the output data and the prior amount of damage;
comparing the cumulative damage estimate at each location in the brain to a threshold that is specific to that location; and
generating an alert when the cumulative damage estimate satisfies the threshold or is projected to satisfy the threshold, the alert indicating a safety warning.

* * * * *